US012807655B2

(12) United States Patent
Schwarz

(10) Patent No.: US 12,807,655 B2
(45) Date of Patent: Nov. 24, 2026

(54) FRAGMENTS OF HLYA AND USES THEREOF

(71) Applicant: NUMAFERM GmbH, Duesseldorf (DE)

(72) Inventor: Christian Schwarz, Duesseldorf (DE)

(73) Assignee: NUMAFERM GmbH, Duesseldorf (DE)

( * ) Notice: Subject to any disclaimer, the term of this patent is extended or adjusted under 35 U.S.C. 154(b) by 973 days.

(21) Appl. No.: 17/912,066

(22) PCT Filed: Mar. 18, 2021

(86) PCT No.: PCT/EP2021/056948
§ 371 (c)(1),
(2) Date: Sep. 16, 2022

(87) PCT Pub. No.: WO2021/185968
PCT Pub. Date: Sep. 23, 2021

(65) Prior Publication Data

US 2023/0144204 A1 May 11, 2023

(30) Foreign Application Priority Data

Mar. 18, 2020 (EP) .................................... 20163961
Apr. 8, 2020 (EP) .................................... 20168779

(51) Int. Cl.
*C12N 15/62* (2006.01)
*C07K 14/245* (2006.01)
*C07K 14/31* (2006.01)
*C12N 15/74* (2006.01)

(52) U.S. Cl.
CPC ............ *C07K 14/245* (2013.01); *C07K 14/31* (2013.01); *C12N 15/62* (2013.01); *C12N 15/74* (2013.01); *C07K 2319/50* (2013.01)

(58) Field of Classification Search
CPC ..................................................... C12N 15/62
See application file for complete search history.

(56) References Cited

FOREIGN PATENT DOCUMENTS

| | | | |
|---|---|---|---|
| EP | 2583975 | A1 | 4/2013 |
| WO | 8706953 | A1 | 11/1987 |
| WO | 2006036406 | A2 | 4/2006 |
| WO | 2011004263 | A2 | 1/2011 |
| WO | 2013057312 | A1 | 4/2013 |
| WO | 2014081884 | A1 | 5/2014 |
| WO | 2014170430 | A1 | 10/2014 |
| WO | 2015049332 | A1 | 4/2015 |

OTHER PUBLICATIONS

UniProt A0A444R917, *E. coli* RTX toxin hemolysin A, 2019. Deposit by Potter et al. Retrieved from < https://rest.uniprot.org/uniprotkb/A0A444R917.txt > on Jan. 9, 2026.*
Benabdelhak et al., "A Specific Interaction Between the NBD of the ABC transporter HlyB and a C-Terminal Fragment of its Transport Substrate Haemolysin A", J. Mol. Biol., 2003, vol. 327, pp. 1169-1179.*
Lecher et al., "An RTX Transporter Tethers Its Unfolded Substrate during Secretion via a Unique N-Terminal Domain", Structure 20, 1778-1787, Oct. 10, 2012.*
UniProt Q1R2T5, Hemolysin A from *E. coli*. Retrieved from < https://www.uniprot.org/uniprotkb/Q1R2T5/entry#sequences > on Mar. 27, 2026.*
Extended European Search Report dated Jun. 4, 2020, from parallel EP Application 20 163 961.4, 7 pages (for reference purposes only).
Extended European Search Report dated Jun. 4, 2020, from parallel EP Application 20 168 779.5, 8 pages (for reference purposes only).
International search report dated Jul. 19, 2021, from parallel PCT Application PCT/EP2021/056948, 16 pages (for reference purposes only).
Sanchez-Magraner et al., "Interdomain Ca2+ effects in Escherichia coli a-haemolysin: Ca2+ binding to the C-terminal domain stabilizes both C- and N-terminal domains", Biochimica et Biophysica Acta, 2010, pp. 1225-1233, vol. 1798, Issue 6, Elsevier B.V.
Altschul et al., "Basic Local Alignment Seach Tool", J. Mol. Biol., 1990, pp. 403-410, 215, Academic Press Limited.
Altschul et al., "Gapped BLAST and PSI-BLAST: a new generation of protein database search programs", Nucleic Acids Research, 1997, pp. 3389-3402, vol. 25, No. 17.
Chenna et al., "Multiple sequence alignment with the Clustal series of programs", Nucleic Acids Research, 2003, pp. 3497-3500, vol. 31, No. 13, Oxford University Press.
Notredame et al., "T-Coffee: A Novel Method for Fast and Accurate Multiple Sequence Alignment", J. Mol. Biol., 2000, pp. 205-217, Academic Press.
Baumann et al., "Three-dimensional structure of the alkaline protease of Pseudomonas aeruginosa: a two-domain protein with a calcium binding parallel beta roll motif", The EMBO Journal, 1993, pp. 3357-3364, vol. 12, No. 9.
Meier et al., "A Calcium-gated Lid and a Large β-Roll Sandwich Are Revealed by the Crystal Structure of Extracellular Lipase from Serratia marcescens", J. Biol. Chem., 2007, pp. 31477-31483, vol. 282, No. 43, The American Society for Biochemistry and Molecular Biology, Inc.
Sambrook et al., "Molecular Cloning, A Laboratory Manual", 1989, Second Edition, Cold Spring Harbor Laboratory Press, 30 pages.
Deangelis et al., "Solid-phase reversible immobilization for the isolation of PCR products", Nucleic Acids Research, 1995, pp. 4742-4743, vol. 23, No. 22, Oxford University Press.
Gibson et al., "Enzymatic assembly of DNA molecules up to several hundred kilobases", Nature Methods, 2009, pp. 343-345, vol. 6 No. 5, Nature America, Inc.
Database UniProtKB/TrEMBL [Online] (May 8, 2019), "RTX toxin hemolysin A {ECO:0000313 EMBL:RXD13418.1}", XP093412635, Database accession No. A0A444R917.

* cited by examiner

*Primary Examiner* — Suzanne M Noakes
(74) *Attorney, Agent, or Firm* — Knobbe, Martens, Olson & Bear, LLP

(57) ABSTRACT

The present disclosure relates to the field of molecular biology, recombinant peptide, and protein expression and relates to amino acid sequences comprising hemolysin A (HlyA) fragments to improve the expression and secretion of a peptide or protein of interest.

14 Claims, 4 Drawing Sheets

Specification includes a Sequence Listing.

| | |
|---|---|
| 10 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 11 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 12 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 13 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 14 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 15 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 16 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 17 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 18 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |
| 19 | MGNSLAKNVLFGGKGNDKLYGSEGADLLDGGEGDDLLKGGYGNDIYRYLSGYGHHIIDDDGGKEDKLSLADIDFRDVAFKREGNDLIAYKAEGNVLSIGHKNGITFRNWF |

Fig. 1 (continued)

FRAGMENTS OF HLYA AND USES THEREOF

REFERENCE TO A SEQUENCE LISTING SUBMITTED VIA EFS-WEB

The content of the ASCII text file of the sequence listing named "P85677US_seq_ST25", which is 68 kb in size was created on Mar. 18, 2020; the sequence listing is electronically submitted via EFS-Web herewith and is herein incorporated by reference in its entirety.

CROSS-REFERENCE TO RELATED APPLICATION

The present application is a national stage entry according to 35 U.S.C. § 371 of PCT application No.: PCT/EP2021/056948 filed on Mar. 18, 2021; which claims priority to European patent application 20163961.4 filed on Mar. 18, 2020 and also claims priority to European patent application 20168779.5 filed on Apr. 8, 2020; all of which are incorporated herein by reference in their entirety and for all purposes.

TECHNICAL FIELD

The present disclosure lies in the field of molecular biology, recombinant peptide and protein expression and relates to amino acid sequences comprising hemolysin A (HlyA) fragments to improve the expression and secretion of a peptide or protein of interest.

BACKGROUND

To date, recombinant protein/enzyme production for use in industrial processes is widely established. It is expected that in the future more and more industrial processes that are currently based on traditional chemistry will be adapted to involve recombinant technologies.

Type 1 secretion systems (T1 SS), which mostly occur in Gram-negative bacteria, have been described as means to allow efficient peptide and protein expression and/or secretion (See, e.g., international patent publications WO 2013/057312 A1 and WO 2014/170430 Among the family of T1 SS the hemolysin (Hly) T1 SS involving HlyA as transport substrate is of particular interest, as it is devoid of any proteolytic activity and thus does not degrade the secreted peptide or protein of interest. The hemolysin (Hly) T1 SS of *E. coli* consists of the inner membrane protein HlyB, which is an ATP binding cassette (ABC) transporter, the outer membrane protein TolC and the membrane fusion protein HlyD in the inner membrane. The interacting substrate HlyA is exported through the hemolysin secretion system in an ATP dependent manner. Both WO 2013/057312 A1 and WO 2014/170430 A1 describe the industrial use of the Hly T1 SS.

While the technologies based on the Hly T1 SS, in particular fusion proteins of peptides and proteins to be expressed with HlyA or a defined fragment thereof termed HlyA1 (SEQ ID NO:1), are known in the art, in particular from the international patent publications cited above, and are commercially available, there still exists need for further optimized methods that allow more efficient production of peptides and proteins.

SUMMARY

Shortened versions of the known HlyA fragment termed "HlyA1" and having the amino acid set forth in SEQ ID NO:1 when fused to a peptide or protein of interest that is to be recombinantly produced by expression of a fusion protein in a host cell provide for similar or increased expression rates and thus allow higher yields of the desired fused product. In this context, it needs to be mentioned that a shortened tag used for expression/secretion is tantamount to an increased yield of the desired product if the net amount stays the same. Therefore, similar yields with a shortened expression tag are also advantageous over those with a longer expression tag.

In a first aspect, an isolated polypeptide may include a first amino acid sequence, wherein the first amino acid sequence (1) is 30 to 202 amino acids in length; and (2) has at least 80%, at least 85%, at least 90%, at least 95%, at least 97.5%, at least 99% or at least 99.5% sequence identity over its entire length with an amino acid sequence comprised in the amino acid sequence set forth in SEQ ID NO:1 (HlyA1), wherein the isolated polypeptide does not include the full amino acid sequence as set forth in SEQ ID NO:1.

In various embodiments, the isolated polypeptide comprises less than 203 continuous amino acids of the amino acid sequence set forth in SEQ ID NO:1.

In some embodiments, the first amino acid sequence is derived from the amino acid sequence set forth in SEQ ID NO:1 by any one or more of an N-terminal truncation, a C-terminal truncation or a deletion of one or more amino acids. In various embodiments, the deletion is a C-terminal deletion and includes deletion of the C-terminally located secretion signal.

In various embodiments, the first amino acid sequence comprises any one or more of the amino acid sequence motifs set forth in SEQ ID NO:2 (GNSLA), SEQ ID NO:3 (LKGGYGNDIYRYLSGYGH), SEQ ID NO:4 (RNWF), SEQ ID NO:5 (RNWFEKESGDISNHQIEQIFDKSGRIITP), SEQ ID NO:6 (LAYGS), SLLQLSGNASDFSYGRNSITL (SEQ ID NO:7), GGKGNDKLY (SEQ ID NO:38), GGEGDDLLK (SEQ ID NO:39), GGYGNDIYR (SEQ ID NO:40), GGKGNDKLYSEGADLLDGGEGDDLLK (SEQ ID NO:41), GGEGDDLLKGGYGNDIYR (SEQ ID NO:42), and GGKGNDKLYG SEGADLLDGGEGDDLLKGGYGNDIYR (SEQ ID NO:43). For example, the first amino acid sequence may comprise the amino acid motif(s) of:

(i) SEQ ID NO: 5;
(ii) SEQ ID Nos. 5 and 6;
(iii) SEQ ID Nos. 5, 6 and 7;
(iv) SEQ ID NO: 3;
(v) SEQ ID Nos. 3 and 4;
(vi) SEQ ID NO: 7;
(vii) SEQ ID Nos. 2 and 3;
(viii) SEQ ID Nos. 2 and 5;
(ix) SEQ ID Nos. 2, 6 and 7;
(x) SEQ ID Nos. 2, 5 and 6;
(xi) SEQ IN Nos. 2, 5, 6 and 7;
(xii) SEQ ID Nos. 2, 3 and 4;
(xiii) SEQ ID Nos. 2, 3 and 5;
(xiv) SEQ ID NO:38;
(xv) SEQ ID NO:39;
(xvi) SEQ ID NO:40;
(xvii) SEQ ID NO:41;
(xviii) SEQ ID NO:42;
(xix) SEQ ID NO:43;
(xx) SEQ ID Nos. 2 and 38;
(xxi) SEQ ID Nos. 2 and 39;
(xxii) SEQ ID Nos. 2 and 40;

(xxiii) SEQ ID Nos. 2 and 41;
(xxiv) SEQ ID Nos. 2 and 42; or
(xxv) SEQ ID Nos. 2 and 43.

In various embodiments, the isolated polypeptide comprises a second amino acid sequence N-terminal or C-terminal to the first amino acid sequence, wherein the second amino acid sequence encodes for at least one peptide or polypeptide of interest. The second amino acid sequence may be linked directly or via a linker sequence to the N- or C-terminal end of the first amino acid sequence. The linker sequence, if present, may be 1 to 30 amino acids in length. In some embodiments, the linker sequence comprises a protease recognition and cleavage site.

In various embodiments, the second amino acid sequence is 2 to 500 amino acids in length, preferably 10 to 200 amino acids in length. The lower limit may also be 12 or 15 amino acids and the upper limit, independently thereof, also 180 or 150 or 100 amino acids.

In some embodiments, the isolated polypeptide further comprises at least one third amino acid sequence, optionally at least one affinity tag.

In various embodiments, the isolated polypeptide has relative to a polypeptide comprising the full length sequence of SEQ ID NO:1 as the first amino acid sequence an equal or increased expression in a host cell under identical expression conditions.

In another aspect, a nucleic acid, nucleic acid molecule or isolated nucleic acid molecule may encode the isolated polypeptide as described herein. In one aspect, said nucleic acid is part of a vector. One aspect thus features a (nucleic acid) vector comprising a nucleic acid molecule. The vector may be an expression vector and may comprise additional nucleic acid sequences necessary to facilitate its function in a host cell.

One further aspect relates to a host cell comprising a nucleic acid molecule or a vector. The host cell may be a prokaryotic host cell, for example an *E. coli* cell.

In a still further aspect, a method for the production of a polypeptide (isolated polypeptide) as described herein, may include (1) cultivating the host cell described herein under conditions that allow the expression of the polypeptide; and
(2) isolating the expressed polypeptide from the host cell.

The method may, in various embodiments, further comprise recovering the expressed peptide or protein from the host cell and/or the culture medium. In some embodiments of the methods described herein, the method further comprises secretion of the expressed recombinant peptide or protein into the culture medium by cultivating the host cell under conditions that allow secretion of the recombinant peptide or protein into the culture medium. To achieve this, the host cell may comprise further nucleic acid molecules that encode for components of a secretion system.

The method may in various embodiments also comprise recovering the expressed peptide or protein from the host cell in form of insoluble protein aggregates, namely inclusion bodies (IBs). In such embodiments, the methods may comprise a step of resolubilizing the peptide/protein and/or reconstituting/refolding it under suitable conditions. In such embodiments, the first amino acid sequence may be a C-terminally truncated version of the HlyA1 reference sequence as set forth in SEQ ID NO:1.

In various embodiments of the methods, (a) the host cell is a prokaryotic cell, for example an *E. coli* cell; and/or (b) the host cell expresses HlyB and HlyD, for example either endogenously or by introduction of exogenous nucleic acid sequences; and/or (c) the expression is performed in minimal culture medium; and/or (d) the culture medium comprises 1-40 mM of $Ca^{2+}$; and/or (e) the expressed recombinant peptide or protein is the recombinant peptide or protein; and/or (f) the recombinant peptide or protein is purified using a method selected from affinity chromatography, ion exchange chromatography, reverse phase chromatography, size exclusion chromatography, and combinations thereof; and/or (g) the method comprises treatment of the recombinant peptide or protein with a protease suitable for cleavage of a protease cleavage site within the recombinant peptide or protein; and/or (h) the method comprises a step as defined in (g) followed by purification of the recombinant peptide or protein.

In still another aspect, an isolated polypeptide may be used for facilitating the expression of a recombinant peptide or protein.

It is understood that all combinations of the above disclosed embodiments are also intended to fall within the scope of the claims.

DETAILED DESCRIPTION

Figure 1:
FIG. 1 shows fragments 1-19 of HlyA1 (SEQ ID NO:1) that were tested in Example 1 for their expression per se and in combination with exemplary peptides of interest having the amino acid set forth in SEQ ID Nos. 28-30. Boxes indicate deleted parts of the HlyA1 reference sequence ("H") as set forth in SEQ ID NO:1. The amino acid sequences of fragments 1-19 are set forth in SEQ ID Nos. 8-26.
Figure 1:
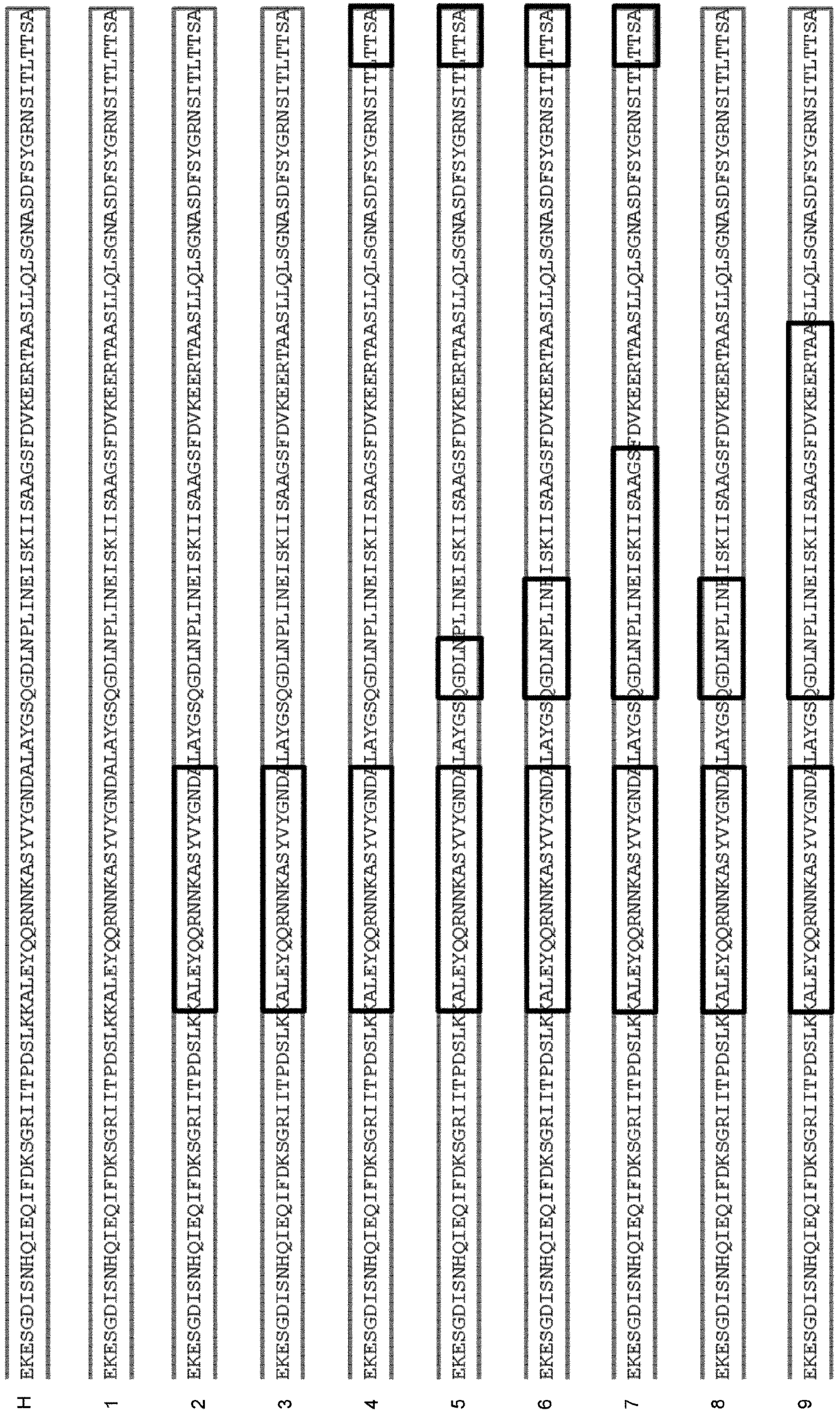
Figure 1:
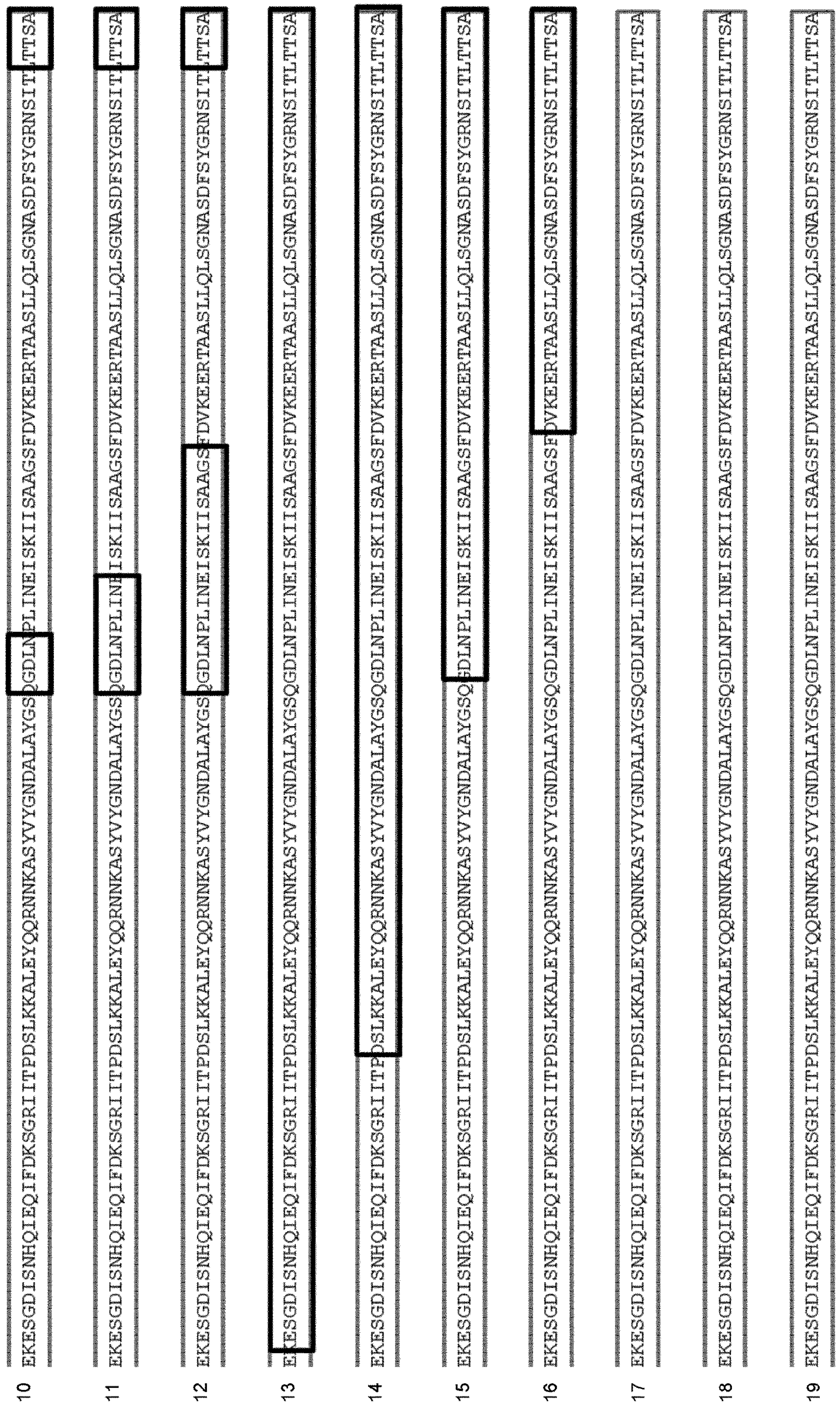

The terms used herein have, unless explicitly stated otherwise, the meanings as commonly understood in the art.

"At least one", as used herein, relates to one or more, in particular 1, 2, 3, 4, 5, 6, 7, 8, 9, 10 or more.

"Isolated" as used herein in relation to a molecule means that said molecule has been at least partially separated from other molecules it naturally associates with or other cellular components. "Isolated" may mean that the molecule has been purified to separate it from other molecules and components, such as other proteins and nucleic acids and cellular debris.

"Nucleic acid" as used herein includes all natural forms of nucleic acids, such as DNA and RNA. Preferably, the nucleic acid molecules are DNA.

The term "peptide" is used throughout the specification to designate a polymer of amino acid residues connected to each other by peptide bonds. A peptide may have 2-100 amino acid residues. The terms "protein" and "polypeptide" are used interchangeably throughout the specification to designate a polymer of amino acid residues connected to each other by peptide bonds. A protein or polypeptide has preferably 100 or more amino acid residues.

The term "an N-terminal fragment" relates to a peptide or protein sequence which is in comparison to a reference peptide or protein sequence C-terminally truncated, such that a contiguous amino acid polymer starting from the N-terminus of the peptide or protein remains. In some embodiments, such fragments may have a length of at least 10 amino acids, at least 20 amino acids, at least 30 amino acids, at least 40 amino acids or at least 45 or at least 50 amino acids.

The term "a C-terminal fragment" relates to a peptide or protein sequence which is in comparison to a reference peptide or protein sequence N-terminally truncated, such that a contiguous amino acid polymer starting from the C-terminus of the peptide or protein remains. In some embodiments, such fragments may have a length of at least 10 amino acids, at least 20 amino acids, at least 30 amino acids, at least 40 amino acids or at least 45 or at least 50 amino acids.

The term "fusion protein" as used herein concerns two or more peptides and proteins which are N- or C-terminally connected to each other, typically by peptide bonds, including via an amino acid/peptide linker sequence. Such fusion proteins may be encoded by two or more nucleic acid sequences which are operably fused to each other. In certain embodiments, a fusion protein refers to at least one peptide or protein of interest C-terminally or N-terminally fused to a first amino acid sequence.

Generally, any nucleotide sequence described herein may comprise an additional start and/or stop codon or that a start and/or stop codon included in any of the sequences described herein may be deleted, depending on the nucleic acid construct used. The skilled person will base this decision, e.g., on whether a nucleic acid sequence comprised in the nucleic acid molecule is to be translated and/or is to be translated as a fusion protein. In various embodiments, the reference sequence and all fragments thereof disclosed herein, may thus comprise an N-terminal M residue directly linked to the N-terminal amino acid given in the respective sequence and encoded by the above-referenced starting codon.

The hemolysin (Hly) secretion system is a protein secretion system which mostly occurs in gram-negative bacteria. This secretion system belongs to the family of type I secretion systems which transport their substrates in an ATP driven manner in a single step from the cytosol to the extracellular space without an intermediate station in the periplasm. The Hly secretion system comprises hemolysin B (HlyB) which represents an ATP-binding cassette (ABC) transporter, the membrane fusion protein hemolysin D (HlyD), and the universal outer membrane protein TolC. The 110 kDa hemolytic toxin hemolysin A (HlyA) is a transport substrate of the Hly secretion system. On genetic level, the components necessary for hemolysin A-specific secretion are organized in an operon structure. The nucleic acid sequence encoding for hemolysin C (HlyC) also forms part of this operon but is not required for HlyA secretion through the Hly secretion system. HlyC catalyzes acylation of HlyA which renders HlyA hemolytic. HlyA is a protein which consists of 1024 amino acid residues and requires for its export via the Hly secretion system its C-terminus comprising about 40-60 amino acids. Furthermore, HlyA is characterized in that it comprises N-terminally to the 40-60 C-terminal amino acids that constitute the secretion signal a domain comprising several glycine rich (GG) repeats (GGXGXDXXX, wherein X can be any amino acid). Glycine rich repeats are the characteristic of the repeats in toxin (RTX) toxin family. The glycine rich repeats bind Ca2+ which induces their folding. Hence, in absence of Ca2+ the domain comprising the glycine rich repeats is typically unstructured.

Shortened fragments of HlyA are equally if not better suited for facilitating the expression of a peptide/protein of interest than the previously used full length HlyA or the known fragment thereof having the amino acid sequence of SEQ ID NO:1. This increased expression is also independent from the presence of the secretion signal and the secretion of the peptide/fusion protein, as C-terminally truncated versions of HlyA that lack the secretion signal similarly provide for increased expression. In the absence of such a secretion signal, the recombinantly expressed protein may, in various embodiments, be enriched in the host cells in form of inclusion bodies (IB) and later recovered therefrom, for example by using techniques described herein below.

Thus, in a first aspect, an isolated polypeptide may include a first amino acid sequence, wherein the first amino acid sequence (1) is 30 to 202 amino acids in length; and (2) has at least 80%, at least 85%, at least 90%, at least 95%, at least 97.5%, at least 99% or at least 99.5% sequence identity over its entire length with an amino acid sequence comprised in the amino acid sequence set forth in SEQ ID NO:1 (HlyA1).

The isolated polypeptide does not include the full amino acid sequence as set forth in SEQ ID NO:1, but is a fragment thereof that may be obtained by truncating the amino acid sequence of SEQ ID NO:1 on its C- and/or N-terminus and/or by deleting part of its sequence. In various embodiments, the isolated polypeptide is a C-terminally truncated version of SEQ ID NO:1.

The first amino acid sequence is 30 to 202 amino acids in length and has, over its entire length, at least 80%, at least 85%, at least 90%, at least 95%, at least 97.5%, at least 99% or at least 99.5% sequence identity with the corresponding part of the amino acid sequence set forth in SEQ ID NO:1.

Determination of the sequence identity of nucleic acid or amino acid sequences can be done by a sequence alignment based on well-established and commonly used BLAST algorithms (See, e.g. Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, S.3389-3402). Such an alignment is based on aligning similar nucleotide or amino acid sequences stretches with each other. Another algorithm known in the art for said purpose is the FASTA-Algorithms. Alignments, in particular multiple sequence comparisons, are typically done by using computer programs. Commonly used are the Clustal series (See, e.g., Chenna et al. (2003): Multiple sequence alignment with the Clustal series of programs. Nucleic Acid Research 31, 3497-3500), T-Coffee (See, e.g., Notredame et al. (2000): T-Coffee: A novel method for multiple sequence alignments. J. Mol. Biol. 302, 205-217) or programs based on these known programs or algorithms.

Also possible are sequence alignments using the computer program Vector NTI® Suite 10.3 (Invitrogen Corporation, 1600 Faraday Avenue, Carlsbad, CA, USA) with the set standard parameters, with the AlignX module for sequence comparisons being based on the ClustalW. If not indicated otherwise, the sequence identity is determined using the BLAST algorithm.

Such a comparison also allows determination of the similarity of the compared sequences. Said similarity is typically expressed in percent identify, i.e. the portion of identical nucleotides/amino acids at the same or corresponding (in an alignment) sequence positions relative to the total number of the aligned nucleotides/amino acids. For example, if in an alignment 90 amino acids of a 100 aa long query sequence are identical to the amino acids in corresponding positions of a template sequence, the sequence identity is 90%. The broader term "homology" additionally considers conserved amino acid substitutions, i.e. amino acids that are similar in regard to their chemical properties, since those typically have similar chemical properties in a protein. Accordingly, such homology can be expressed in percent homology. If not indicated otherwise, sequence identity and sequence homology relate to the entire length of the aligned sequence.

The feature that an amino acid position corresponds to a numerically defined position in SEQ ID NO:1 means that the respective position correlates to the numerically defined position in SEQ ID NO:1 in an alignment obtained as described above.

The first amino acid sequence is, in various embodiments, 30 to 202 amino acids in length. The lower limit may be 35, 40, or 45 amino acids in length, while the upper limit may be 200, 190, 180, 170, 160, 150, 140 amino acids in length or less. It may be preferred that the first amino acid sequence is as short as possible, as long as its beneficial influence on expression levels is not impaired. Generally, the skilled person will know how to find a balance between a sequence that is as short as possible while still providing for the desired expression levels.

While the first amino acid sequence may correspond to a continuous amino acid stretch of the amino acid sequence set forth in SEQ ID NO:1 having the indicated length, it is similarly possible that the first amino acid sequence corresponds to discontinuous stretches of the amino acid sequence set forth in SEQ ID NO:1, for example if it corresponds to stretches of SEQ ID NO:1 with certain amino acids or amino acid sequences being deleted therefrom. The first amino acid sequence may thus be derived from the amino acid sequence set forth in SEQ ID NO:1 by any one or more of an N-terminal truncation, a C-terminal truncation or a deletion of one or more amino acids.

It has been found that the first amino acid sequence performs particularly well, if it comprises any one or more of the amino acid sequence motifs GNSLA (SEQ ID NO:2), LKGGYGNDIYRYLSGYGH (SEQ ID NO:3), RNWF (SEQ ID NO:4), RNWFEKESGDISNHQIEQIFDKSGRIITP (SEQ ID NO:5), LAYGS (SEQ ID NO:6), SLLQLSGNASDFSYGRNSITL (SEQ ID NO:7), GGKGNDKLY (SEQ ID NO:38), GGEGDDLLK (SEQ ID NO:39), GGYGNDIYR (SEQ ID NO:40), GGKGNDKLYSEGADLLD GGEGDDLLK (SEQ ID NO:41), GGEGDDLLKGGYGNDIYR (SEQ ID NO:42), and GGKGNDKLYG SEGADLLDGGEGDDLLKGGYGNDIYR (SEQ ID NO:43).

The above motifs can be present individually or in combination in the first amino acid sequence. In various embodiments, the first amino acid sequence therefore comprises or consists essentially of the amino acid motif(s) of:

(i) SEQ ID NO: 5;
(ii) SEQ ID Nos. 5 and 6;
(iii) SEQ ID Nos. 5, 6 and 7;
(iv) SEQ ID NO: 3;
(v) SEQ ID Nos. 3 and 4;
(vi) SEQ ID NO: 7;
(vii) SEQ ID Nos. 2 and 3;
(viii) SEQ ID Nos. 2 and 5;
(ix) SEQ ID Nos. 2, 6 and 7;
(x) SEQ ID Nos. 2, 5 and 6;
(xi) SEQ IN Nos. 2, 5, 6 and 7;
(xii) SEQ ID Nos. 2, 3 and 4;
(xiii) SEQ ID Nos. 2, 3 and 5;
(xiv) SEQ ID NO:38;
(xv) SEQ ID NO:39;
(xvi) SEQ ID NO:40;
(xvii) SEQ ID NO:41;
(xviii) SEQ ID NO:42;
(xix) SEQ ID NO:43;
(xx) SEQ ID Nos. 2 and 38;
(xxi) SEQ ID Nos. 2 and 39;
(xxii) SEQ ID Nos. 2 and 40;
(xxiii) SEQ ID Nos. 2 and 41;
(xxiv) SEQ ID Nos. 2 and 42; or
(xxv) SEQ ID Nos. 2 and 43.

In various embodiments, the first amino acid sequence comprises at least SEQ ID NO:2. In other embodiments, the first amino acid sequence comprises at least SEQ ID NO:5. In still further embodiments, the first amino acid sequence comprises at least SEQ ID NO:7. In still further embodiments, the first amino acid sequence comprises at least any one of SEQ ID Nos:38-43. In various embodiments, it comprises (i) SEQ ID NO:2 and SEQ ID NO:5 or (ii) SEQ ID NO:5 and SEQ ID NO:7; or (iii) SEQ ID NO:2 and any one of SEQ ID Nos. 38-43.

It has been found that in particular those first amino acid sequences that comprise the sequence motif of SEQ ID NO:2, optionally in combination with at least one GG repeat sequence (as set forth in SEQ ID Nos. 38-40) or the sequence motif set forth in SEQ ID NO:5 consistently provide for good expression results if they are used as an expression tag in a fusion protein construct.

In various embodiments, the first amino acid sequence lacks the 4 C-terminal amino acids of HlyA1 (SEQ ID NO:27; TTSA). It has been found that such first amino acid sequences that lack the C-terminal amino acids of SEQ ID NO:1 consistently provide for good expression results if used as an expression tag in a fusion protein construct. In addition to these 4 C-terminal amino acids, additional 1, 2, 3, 4, 5, 6, 7, 8, 9, 10, 11, 12, 13, 14, 15, 16, 17, 18, 19, 20, 21, 22, 23, 24, 25, or 26 amino acids from the C-terminus of SEQ ID NO:1 may be deleted.

In some embodiments, the first amino acid sequence comprises SEQ ID NO:2 and/or lacks the sequence of SEQ ID NO:27. In various embodiments, such first amino acid sequences may lack further amino acids from the C-terminus of SEQ ID NO:1, for example up to 30 amino acids, or may lack the amino acids corresponding to amino acids 135-218, 130-218, 125-218, 120-218, 115-218, 110-218, 105-218, 100-218, 95-218, 90-218, 85-218, 80-218, 75-218, 70-218, 65-218, 60-218, 55-218, 50-218, 45-218 or 40-218 of SEQ ID NO:1, the amino acid sequence of such fragments being set forth in SEQ ID Nos. 44-63, respectively, and all deletions up to residue 40 using the positional numbering of SEQ ID NO:1. In addition, in various embodiments wherein the first amino acid sequence comprises SEQ ID NO:2 and preferably any one of SEQ ID Nos. 38-43, any one or more of the amino acids up to the position corresponding to position 109 of SEQ ID NO:1 (starting from 218 and counting backwards) may be deleted, thus effectively covering deletion of all positions indicated herein. Such deletions may cover the amino acid residues at the positions corresponding to positions 185-218, positions 165-218, positions 135-218 or positions 110-218 of SEQ ID NO:1. Also encompassed are any deletions of ranges between those recited above, such as 184-218, 183-218, 182-218, 181-218, 180-218, 179-218, 178-218, 177-218, 176-218, 175-218, 174-218, 173-218, 172-218, 171-218, 170-218, 169-218, 168-218, 167-218, 166-218, 165-218, 164-218, 163-218, 162-218, 161-218, 160-218, 159-218, 158-218, 157-218, 156-218, 155-218, 154-218; 153-218; 152-218; 151-218; 150-218; 149-218; 148-218; 147-218; 146-218; 145-218; 144-218; 143-218; 142-218; 141-218; 140-218; 139-218; 138-218; 137-218; 136-218; 134-218; 133-218; 132-218; 131-218; 130-218; 129-218; 128-218; 127-218; 126-218;

125-218; 124-218; 123-218; 122-218; 121-218; 120-218; 119-218; 118-218; 117-218; 116-218; 115-218; 114-218; 113-218; 112-218; and 111-218. Furthermore, deletions of the amino acids at the positions corresponding to positions 215-218 of SEQ ID NO:1 may be combined with deletions at the positions corresponding to positions 165-182, such as 165-168, 165-169, 165-170, 165-171, 165-172, 165-173, 165-174, 165-175, 165-176, 165-177, 165-178, 165-179, 165-180, and 165-181. In various embodiments, the fragments of the amino acid sequence set forth in SEQ ID NO:1 include at least amino acids at positions corresponding to positions 10-40 of SEQ ID NO:1, preferably 10-45, 10-50, 10-55, 1-40, 1-45, 1-50, 1-55, 1-60, 1-65, or 1-68, for example 1-75, 1-90, 1-100, 1-105 or 1-109 of SEQ ID NO:1. In various embodiments, the first amino acid sequence is thus a fragment of SEQ ID NO:1 that has a C-terminal truncation, for example of amino acids in the positions corresponding to positions 215-218, 214-218, 185-218, 165-218, 135-218, or 111-218 of SEQ ID NO:1. In various embodiments the C-terminal end up to amino acid 110 (not including 110) in the numbering of SEQ ID NO:1 may be truncated. In various other embodiments, the amino acids in positions corresponding to positions 215-218 or 214-218 of SEQ ID NO:1 and additionally in the positions corresponding to positions 164-168, 165-168, 164-173, 165-173, 164-183, 165-183 or 165-182 of SEQ ID NO:1 may be deleted. In various embodiments any continuous 4 or more amino acids in the region corresponding to positions 164-183 of SEQ ID NO:1, in particular starting from position 164 or 165 and up to position 182 or 183 may be deleted. Exemplary embodiments of such truncations are set forth in SEQ ID Nos. 65-71.

In various other embodiments, the first amino acid sequence may also comprise the following sequence motifs: SEQ ID NO:2 and SEQ ID NO:4; SEQ ID NO:2 and SEQ ID NO:6; SEQ ID NO:2 and SEQ ID NO:7; SEQ ID NO:3 and SEQ ID NO:5, SEQ ID NO:3 and SEQ ID NO:6; SEQ ID NO:3 and SEQ ID NO:7; SEQ ID NO:4 and SEQ ID NO:6; SEQ ID NO:4 and SEQ ID NO:7; SEQ ID NO:6 and SEQ ID NO:7; SEQ ID Nos:2, 3 and 4; SEQ ID Nos. 2, 3 and 5; SEQ ID Nos. 2, 3 and 6; SEQ ID Nos. 2, 3 and 7; SEQ ID Nos. 2, 4 and 6; SEQ ID Nos. 2, 4 and 7; SEQ ID Nos. 2, 5 and 7; SEQ ID Nos. 3, 4 and 6; SEQ ID Nos. 3, 4 and 7; SEQ ID Nos. 3, 5 and 6; SEQ ID Nos. 3, 5 and 7; SEQ ID Nos. 4, 6 and 7; SEQ ID Nos. 2, 3, 4 and 6; SEQ ID Nos. 2, 3, 4 and 7; SEQ ID Nos. 2, 3, 5 and 6; SEQ ID Nos. 2, 3, 5 and 7; SEQ ID Nos. 2, 4, 6 and 7; SEQ ID Nos. 3, 4, 6 and 7; and SEQ ID Nos. 3, 5, 6 and 7. In various embodiments, the first amino acid sequence may also comprise the following sequence motifs: SEQ ID NO:2 and any one of SEQ ID Nos. 38-43. In all the above embodiments, the C-terminus of SEQ ID NO:1, in particular the 4 most C-terminal amino acids TTSA (SEQ ID NO:27) may be missing.

In various embodiments, the first amino acid sequence comprises a deletion relative to SEQ ID NO:1. In various embodiments, the first amino acid sequence does not comprise any one of the full amino acid sequences of SEQ ID Nos. 46-50 as set forth in WO 2013/057312 A1. In various other embodiments, the first amino acid sequence does not comprise any one of the full amino acid sequences of SEQ ID Nos. 33, 34, 36 of EP 2 583 975 A1, as well as SEQ ID Nos. 4 and 7 of WO 2006/036406 A2 and EPOP:A12703 (200 aa long C-terminal fragment of HlyA) of WO 8706953 A1.

In various embodiments, the first amino acid sequence comprises at least one GG repeat sequence of SEQ ID NO:1. "GG repeat" as used herein, relates to the consensus sequence GGxGxDxUx, wherein x can be any amino acid and U is a hydrophobic, large amino acid, such as F, W, Y, I, L, M. SEQ ID NO:1 comprises 3 such GG repeats in its sequence. These span residues 11-19, 29-37, and 38-46 of SEQ ID NO:1 and have the sequences GGKGNDKLY (SEQ ID NO:38), GGEGDDLLK (SEQ ID NO:39) and GGYGNDIYR (SEQ ID NO:40). Another glycine-rich sequence spans amino acids 60-67 of SEQ ID NO:1 (GGKEDKLS; SEQ ID NO:72) and may also be comprised in the first amino acid sequence. In some embodiments, the first amino acid sequence comprises the GG repeat sequence(s) comprised in any one of SEQ ID Nos:3 (LKGGYGNDIYRYLSGYGH) and 38-43. While the GG repeat may in some embodiments help to facilitate refolding of the polypeptide either after secretion or purification, in cases where no refolding is desired or necessary, the first amino acid sequence does not need to comprise a GG repeat sequence. The expression level as such is not necessarily influenced by the presence or absence of a GG repeat sequence.

It is understood that if the first amino acid sequence comprises any one of the indicated sequences it may comprise further amino acids that may correspond to other motifs or other amino acids not in the recited motifs but corresponding to flanking sequences as defined by SEQ ID NO:1.

The isolated polypeptide typically comprises a second amino acid sequence N-terminal or C-terminal to the first amino acid sequence, wherein the second amino acid sequence encodes for at least one peptide or polypeptide of interest. The second amino acid sequence may be 2 to 500 amino acids in length, preferably 10, 12 or 15 to 200, 180, 150, 120 or 100 amino acids in length.

In various embodiments, the first amino acid sequence comprises the sequence set forth in any one of SEQ ID Nos. 8-26 or 44-63 or 65-71. In further embodiments, also encompassed are variants of these sequences that have at least 80%, at least 85%, at least 90%, at least 95%, at least 97.5%, at least 99% or at least 99.5% sequence identity with the amino acid sequence set forth in the respective template sequence of any one of SEQ ID Nos. 8-26 and 44-63 or 65-71. These variants include truncated versions thereof, for example N- or C-terminal truncations, preferably C-terminal truncations, with these truncations typically being 1-10, preferably 1-5 amino acids in length. The sequence set forth in SEQ ID NO:63 is typically not further truncated.

In various embodiments, the peptide or protein of interest may comprise two or more naturally occurring peptides or proteins, the two or more peptides or proteins may be separated by protease cleavage sites. This also includes embodiments, where the same peptide or protein is included multiple times in said second amino acid sequence. This then allows production of higher amounts of the respective peptide or protein of interest. In other embodiments, the peptide or protein of interest is only a single peptide or protein.

Generally, any peptide or protein may be chosen as protein of interest. In certain embodiments, the protein of interest is a protein, which does not form a homo-dimer or homo-multimer. The avoidance of self-interacting peptides or proteins may be advantageous if the recombinant peptide or protein is to be secreted into the cell culture supernatant, because the formation of larger protein complexes may disturb an efficient protein export. However, the protein of interest may also be a peptide or protein which is a subunit of a larger peptide or protein complex. Such a peptide or protein may be isolated after expression and optionally secretion and be suitable for an in vitro reconstitution of the multi peptide or protein complex. In certain embodiments, the protein or peptide of interest is a protein or peptide having less than 500 amino acid residues, for example less than 200 amino acids or less than 150 amino acids. If these peptides comprise pre- and/or pro-sequences in their native state after translation the nucleic acid sequence encoding for the peptide of interest may be engineered to be limited to the sequence encoding the mature peptide. One exemplary peptide is insulin, e.g., human insulin. The expression of over-expressed peptides and proteins as inclusion bodies is especially advantageous where the peptide or protein is harmful to the host cell. Lipases and proteases are known to be toxic to the host cell and thus the expression of these proteins by the claimed systems and methods are advantageous.

In various embodiments, the peptide or protein of interest is an enzyme. The International Union of Biochemistry and Molecular Biology has developed a nomenclature for enzymes, the EC numbers; each enzyme is described by a sequence of four numbers preceded by "EC". The first number broadly classifies the enzyme based on its mechanism.

Accordingly, a peptide or protein of interest may be chosen from any of the classes EC 1 (Oxidoreductases), EC 2 (Transferases), EC 3 (Hydrolases), EC 4 (Lyases), EC 5 (Isomerases), and EC 6 (Ligases), and the subclasses thereof.

In certain embodiments, the peptide or protein of interest is cofactor dependent or harbors a prosthetic group. For expression of such peptides or proteins, in some embodiments, the corresponding cofactor or prosthetic group may be added to the culture medium during expression.

In certain cases, the peptide or protein of interest is a dehydrogenase or an oxidase. In case the peptide or protein of interest is a dehydrogenase, in some embodiments, the peptide or protein of interest is chosen from the group consisting of alcohol dehydrogenases, glutamate dehydrogenases, lactate dehydrogenases, cellobiose dehydrogenases, formate dehydrogenases, and aldehydes dehydrogenases. In case the peptide or protein of interest is an oxidase, in some embodiments, the peptide or protein of interest is chosen from the group consisting of cytochrome P450 oxidoreductases, in particular P450 BM3 and mutants thereof, peroxidases, monooxygenases, hydrogenases, monoamine oxidases, aldehydes oxidases, xanthin oxidases, amino acid oxidases, and NADH oxidases.

In further embodiments, the peptide or protein of interest is a transaminase or a kinase. In case the peptide or protein of interest is a transaminase, in some embodiments, the peptide or protein of interest is chosen from the group consisting of alanine aminotransferases, aspartate aminotransferases, glutamate-oxaloacetic transaminases, histidinol-phosphate transaminases, and histidinol-pyruvate transaminases. In various embodiments, if the peptide or protein of interest is a kinase, the peptide or protein of interest is chosen from the group consisting of nucleoside diphosphate kinases, nucleoside monophosphate kinases, pyruvate kinase, and glucokinases. In some embodiments, if the peptide or protein of interest is a hydrolase, the peptide or protein of interest is chosen from the group consisting of lipases, amylases, proteases, cellulases, nitrile hydrolases, halogenases, phospholipases, and esterases.

In certain embodiments, if the peptide or protein of interest is a lyase, the peptide or protein of interest is chosen from the group consisting of aldolases, e.g., hydroxynitrile lyases, thiamine-dependent enzymes, e.g., benzaldehyde lyases, and pyruvate decarboxylases. In various embodiments, if the peptide or protein of interest is an isomerase, the peptide or protein of interest is chosen from the group consisting of isomerases and mutases.

In some embodiments, if the peptide or protein of interest is a ligase, the peptide or protein of interest may be a DNA ligase.

In certain embodiments, the peptide or protein of interest may be an antibody. This may include a complete immunoglobulin or fragment thereof, which immunoglobulins include the various classes and isotypes, such as IgA, IgD, IgE, IgGI, IgG2a, IgG2b and IgG3, IgM, etc. Fragments thereof may include Fab, Fv and F(ab')2, Fab', the variable domain of the light chain (VL) or the variable domain of the heavy chain (VH) and related fragments, such as nanobodies, and the like.

Also contemplated herein are therapeutically active peptides and proteins of interest, e.g., cytokines.

Thus, in certain embodiments the peptide or protein of interest is selected from the group consisting cytokines, in particular human or murine interferons, interleukins (IL-1, IL-2, IL-3, IL-4; IL-5; IL-6; IL-7; IL-8; IL-9; IL-10; IL-11; IL-12; IL-13; IL-14; IL-15; IL-16; and IL-17), colony-stimulating factors, necrosis factors, e.g., tumor necrosis factor, such as TNF alpha, and growth factors, such as transforming growth factor beta family members, such as TGF-beta1; TGF-beta2 and TGF-beta3.

In some embodiments, if the peptide or protein of interest is an interferon, the peptide or protein of interest may be selected from the group consisting of interferon alpha, e.g., alpha-1, alpha-2, alpha-2a, and alpha-2b, alpha-2, alpha-16, alpha 21, beta, e.g., beta-1, beta-1a, and beta-1b, or gamma.

In further embodiments, the peptide or protein of interest is an antimicrobial peptide, in particular a peptide selected from the group consisting of bacteriocines and lantibiotics, e.g., nisin, cathelicidins, defensins, and saposins.

Also disclosed herein are peptides or proteins of interest which are therapeutically active peptides or proteins. In certain embodiments, the peptide or protein of interest is a therapeutically active peptide. In some embodiments, a therapeutically active peptide may be selected from the group consisting of Fuzeon/T20, human calcitonin, salmon calcitonin, human corticotropin release factor, Mab40, Mab42, peptides associated with Alzheimer's disease, exenatide, Tesamorelin, Teriparatide, BMP-2, Corticorelin ovine triflutate, Linaclotide, Nesiritide, Lucinactant, Bivalirudin, Lepirudin, Thymalfasin, Glatiramer, Glucagon, Aviptadil, Secretin, Thymosin-b4, Teduglutide, GLP-1, GLP-2 and analoga, Plecanatide, Ecallantide, Anakinra, Disiteritide, Lixisenatide, Liraglutide, Semaglutide, Abaloparatide, Goserelin, Lanreotide, Carfilzomib, Enfuvirtide, T-20, Terlipressin, Elcatonin, Afamelanotide, Oxodotreotide, Caspofungin, Colistin, Polymyxin E, Cyclosporine, Dactinomcyin, Lyovac-Cosmegen, Degarelix, Vancomycin, Secretin, Ziconotide, Gonadorelin, Somastatin, Sincalide, Eptifibatid, Vapreotide, Triptorelin, Desmopressin, Lypressin, Atosiban, Pramintide, Pasireotide, Sandostatin, and Icatibant. The afore-mentioned peptides may be of mammalian or human origin. Also encompassed are analogues of the afore-mentioned peptides that originate from other species, for example homologues from other animals, microorganisms, virus and others.

In certain embodiments, the peptide or protein of interest is a type I secretion substrate. More than 1000 proteins are annotated or have been described as type I secretion substrates in the literature. Many of them have interesting characteristics for the biotechnological usage, in particular proteases and lipases. Suitable proteases and lipases have been described by Baumann et al. (1993) EMBO J 12, 3357-3364; and Meier et al. (2007) J. BIOL. CHEM.: 282(43), pp. 31477-31483. The content of each of these documents is incorporated by reference herein in its entirety.

In certain embodiments, the second amino acid sequence is a peptide or protein of interest which is chosen from the group consisting of MBP, lipase CalB, protease SprP, hydrolase PlaB, hydrolase PlaK, hydrolase PlbF, lipase TesA, Vif, human interferon alpha-1, alpha-2, alpha-8, alpha-16, alpha-21, human interferon beta, human interferon gamma, murine interferon alpha, murine interferon gamma, IFABP, Cas2, affibody protein ZA3, nisin, corticotropin release factor, amyloid-beta peptide, exenatide, Fuzeon/T20, salmon calcitonin, Mab40, Mab42, lipase LipA, SprP, the HIV-1 protein Vif, human calcitonin, Tesamorelin, Teriparatide, BMP-2, Corticorelin ovine triflutate, Linaclotide, Nesiritide, Lucinactant, Bivalirudin, Lepirudin, Thymalfasin, Glatiramer, Glucagon, Aviptadil, Secretin, Thymosin-b4, Teduglutide, GLP-1, GLP-2 and analoga, Plecanatide, Ecallantide, Anakinra, Disiteritide, Lixisenatide, Liraglutide, Semaglutide, Abaloparatide, Goserelin, Lanreotide, Carfilzomib, Enfuvirtide, T-20, Terlipressin, Elcatonin, Afamelanotide, Oxodotreotide, Caspofungin, Colistin, Polymyxin E, Cyclosporine, Dactinomcyin, Lyovac-Cosmegen, Degarelix, Vancomycin, Secretin, Ziconotide, Gonadorelin, Somastatin, Sincalide, Eptifibatid, Vapreotide, Triptorelin, Desmopressin, Lypressin, Atosiban, Pramintide, Pasireotide, Sandostatin, and Icatibant.

The second amino acid sequence may be directly or via a linker sequence linked to the first amino acid sequence. It may be located N- or C-terminally relative to the first amino acid sequence, typically, for example but without limitation, if secretion is not desired or necessary, C-terminally. This means that the N-terminus of the second amino acid sequence is linked, optionally via a linker sequence, to the C-terminus of the first amino acid sequence. However, in other embodiments, the C-terminus of the second amino acid sequence may be fused, optionally via a linker sequence, to the N-terminus of the first amino acid sequence. This latter embodiment may, for example but without limitation, be used, if secretion is desired and the HlyA1 fragment has an intact C-terminal secretion sequence.

In various embodiments, the linker sequence that connects the first and second amino acid sequences is also a peptide sequence and connected to the respective ends of the first and second amino acid sequence via a peptide bond. In various embodiments, the linker sequence may be 1 to 50 amino acids in length, for example 1 to 30 amino acids or 4 to 20, 5 to 15, 5 to 10 or 5 to 8 amino acids.

The linker sequence may be functional in that it may provide for easy cleavage and separation of the first and second amino acid. To facilitate such a purpose, it can comprise or consist of a protease recognition and cleavage site. The linker may also comprise both, a linker sequence that serves only as a link and a protease cleavage site. The linker sequence may be a G-rich sequence, for example a sequence that comprises 4 or 5 consecutive G residues, preferably followed by a S residue.

The term "protease (recognition and) cleavage site" refers to a peptide sequence which can be cleaved by a selected protease thus allowing the separation of peptide or protein sequences which are interconnected by a protease cleavage site. In certain embodiments the protease cleavage site is selected from the group consisting of a Factor Xa, a tobacco edge virus (TEV) protease, a enterokinase, a SUMO Express protease, an Arg-C proteinase, an Asp-N endopeptidases, an Asp-N endopeptidase+N-terminal Glu, a caspase 1, a caspase 2, a caspase 3, a caspase 4, a caspase 5, a caspase 6, a caspase 7, a caspase 8, a caspase 9, a caspase 10, a chymotrypsin-high specificity, a chymotrypsin-low specificity, a clostripain (Clostridiopeptidase B), a glutamyl endopeptidase, a granzyme B, a pepsin, a proline-endopeptidase, a proteinase K, Welqut protease, Clean Cut protease, a staphylococcal peptidase I, a Thrombin, a Trypsin, inteins, SprB from *Staphylococcus aureus*, and a Thermolysin cleavage site. In various embodiments, it may be a Factor Xa, SprB or TEV protease cleavage site. It can be preferred, in some embodiments, to design the protease recognition site such that as few amino acids as possible of the recognition and cleavage site remain attached to the peptide or protein of interest. In various embodiments, a protease recognition and cleavage site is included, the site being for example a TEV protease recognition and cleavage site. The TEV protease cleavage site typically comprises the amino acid sequence ENLYFQG/S (SEQ ID NO:64) and cleaves between the Gln (Q) and Gly/Ser (GIS) residues. In various embodiments, the P1' amino acids may be A, M or C instead of G or S.

In various embodiments, the isolated polypeptide may further comprise at least one third amino acid sequence, for example an affinity tag.

The term "affinity tag" as used herein relates to entities which are coupled to a molecule of interest and allow enrichment of the complex between the molecule of interest and the affinity tag using an affinity tag receptor. In certain embodiments affinity tags may be selected from the group consisting of the Strep-Tag® or Strep-Tag® II, the myc-tag, the FLAG-tag, the His-tag, the small ubiquitin-like modifier (SUMO) tag, the covalent yet dissociable NorpD peptide (CYD) tag, the heavy chain of protein C (HPC) tag, the calmodulin binding peptide (CBP) tag, or the HA-tag or proteins such as Streptavidin binding protein (SBP), maltose binding protein (MBP), and glutathione-S-transferase.

In various embodiments, the isolated polypeptide has relative to a polypeptide comprising the full length sequence of SEQ ID NO:1 as the first amino acid sequence an equal or increased expression in a host cell under identical expression conditions. "Equal", as used in this connection, includes expression levels that are within 20%, preferably within 10%, of the yields achieved with SEQ ID NO:1 as the first amino acid sequence. In various embodiments, this equal or increased expression is tantamount to an increased peptide to fusion protein mass ratio. By shortening the expression tag, similar expression levels still mean a higher yield of the peptide of interest.

In various embodiments, the first amino acid sequence comprises as the first, N-terminal amino acid the residue M. If this is not present within the specific sequences disclosed herein, it may be artificially added, if desired, in particular to facilitate expression in a host cell.

The nucleic acid, in particular the isolated nucleic acid molecule, may encode the polypeptide as described above. The polypeptide comprises the first amino acid sequence and optionally the second amino acid sequence and also optionally at least one third amino acid sequence. All of these amino acid sequences are typically linked by peptide bonds and expressed as a single fusion protein. To facilitate said expression, the nucleic acid molecule comprises a first nucleotide sequence encoding the first amino acid sequence and optionally a second, third and further nucleotide sequence encoding the second, third and further amino acid sequence, with said nucleotide sequences being operably linked to allow expression of the single fusion protein comprising all afore-mentioned amino acid sequences.

The term "operably linked" in the context of nucleic acid sequences means that a first nucleic acid sequence is linked to a second nucleic acid sequence such that the first nucleic acid sequence is placed in a functional relationship with the second nucleic acid sequence. For instance, a promoter sequence is operably linked to a coding sequence of a heterologous gene if the promoter can initiate the transcription of the coding sequence. In a further context, a sequence encoding for the first amino acid sequence is linked such to a second amino acid sequence encoding for a peptide or protein of interest, that if the two sequences are translated a single peptide/protein chain is obtained.

In certain embodiments, the above defined nucleic acid molecules may be comprised in a vector, for example a cloning or expression vector. Generally, the nucleic acid molecules can also be part of a vector or any other kind of cloning vehicle, including, but not limited to a plasmid, a phagemid, a phage, a baculovirus, a cosmid, or an artificial chromosome. Generally, a nucleic acid molecule disclosed in this application may be "operably linked" to a regulatory sequence (or regulatory sequences) to allow expression of this nucleic acid molecule.

Such cloning vehicles can include, besides the regulatory sequences described above and a nucleic acid sequence, replication and control sequences derived from a species compatible with the host cell that is used for expression as well as selection markers conferring a selectable phenotype on transformed or transfected cells. Large numbers of suitable cloning vectors are known in the art, and are commercially available.

In certain embodiments the nucleic acid molecules disclosed herein are comprised in a cloning vector. In some embodiments the nucleic acid molecules disclosed herein are comprised in an expression vector. The vectors may comprise regulatory elements for replication and selection markers. In certain embodiments, the selection marker may be selected from the group consisting of genes conferring ampicillin, kanamycin, chloramphenicol, tetracycline, blasticidin, spectinomycin, gentamicin, hygromycin, and zeocin resistance. In various other embodiments, the selection may be carried out using antibiotic-free systems, for example by using toxin/antitoxin systems, cer sequence, triclosan, auxotrophies or the like. Suitable methods are known to those skilled in the art.

The above-described nucleic acid molecule, comprising a nucleic acid sequence encoding for a protein of interest, if integrated in a vector, must be integrated such that the peptide or protein of interest can be expressed. Therefore, a vector comprises sequence elements which contain information regarding to transcriptional and/or translational regulation, and such sequences are "operably linked" to the nucleotide sequence encoding the polypeptide. An operable linkage in this context is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

In various embodiments, a vector comprising a nucleic acid molecule can therefore comprise a regulatory sequence, preferably a promoter sequence. In certain embodiments, the promoter is identical or homologous to promoter sequences of the host genome. In such cases endogenous polymerases may be capable to transcribe the nucleic acid molecule sequence comprised in the vector. In various embodiments, the promoter is selected from the group of weak, intermediate and strong promoters, preferably from weak to intermediate promoters.

In another preferred embodiment, a vector comprising a nucleic acid molecule comprises a promoter sequence and a transcriptional termination sequence. Suitable promoters for prokaryotic expression are, for example, the araBAD promoter, the tet-promoter, the lacUV5 promoter, the CMV promo tor, the EF1 alpha promotor, the AOX1 promotor, the tac promotor, the T7 promotor, or the lac promotor. Examples of promoters useful for expression in eukaryotic cells are the SV40 promoter or the CMV promoter. Furthermore, a nucleic acid molecule can comprise transcriptional regulatory elements, e.g., repressor elements, which allow regulated transcription and translation of coding sequences comprised in the nucleic acid molecule. Repressor element may be selected from the group consisting of the Lac-, AraC-, or MalR-repressor.

The vector may be effective for prokaryotic or eukaryotic protein expression. In particular, the nucleic acid molecules may be comprised in a vector for prokaryotic protein expression. Such vector sequences are constructed such that a sequence of interest can easily be inserted using techniques well known to those skilled in the art. In certain embodiments, the vector is selected from the group consisting of a pET-vector, a pBAD-vector, a pK184-vector, a pMONO-vector, a pSELECT-vector, pSELECT-Tag-vector, a pVITRO-vector, a pVIVO-vector, a pORF-vector, a pBLAST-vector, a pUO-vector, a pDUO-vector, a pZERO-vector, a pDeNy-vector, a pDRIVE-vector, a pDRIVE-SEAP-vector, a HaloTag® Fusion-vector, a pTARGET™-vector, a Flexi®-vector, a pDEST-vector, a pHIL-vector, a pPIC-vector, a pMET-vector, a pPink-vector, a pLP-vector, a pTOPO-vector, a pBud-vector, a pCEP-vector, a pCMV-vector, a pDisplay-vector, a pEF-vector, a pFL-vector, a pFRT-vector, a pFastBac-vector, a pGAPZ-vector, a pIZ/V5-vector, a p3S-vector, a pIAR-vector, a pSU2726-vector, a pLenti6-vector, a pMIB-vector, a pOG-vector, a pOpti-vector, a pREP4-vector, a pRSET-vector, a p SCREEN-vector, a pSecTag-vector, a pTEFI-vector, a pTracer-vector, a pTrc-vector, a pUB6-vector, a pVAXI-vector, a pYC2-vector, a pYES2-vector, a pZeo-vector, a pcDNA-vector, a pFLAG-vector, a pTAC-vector, a pT7-vector, a Gateway®-vector, a pQE-vector, a pLEXY-vector, a pRNA-vector, a pPK-vector, a pUMVC-vector, a pLIVE-vector, a pCRUZ-vector, a Duet-vector, and other vectors or derivatives thereof.

The vectors may be chosen from the group consisting of high, medium and low copy vectors.

The above described vectors may be used for the transformation or transfection of a host cell in order to achieve expression of a peptide or protein which is encoded by an above described nucleic acid molecule and comprised in the vector DNA. Thus, in a further aspect, a host cell may include a vector or nucleic acid molecule as disclosed herein.

Also contemplated herein are host cells, which comprise a nucleic acid molecule as described herein integrated into their genomes. The skilled person is aware of suitable methods for achieving the nucleic acid molecule integration. For example, the molecule may be delivered into the host cells by means of liposome transfer or viral infection and afterwards the nucleic acid molecule may be integrated into the host genome by means of homologous recombination. In certain embodiments, the nucleic acid molecule is integrated at a site in the host genome, which mediates transcription of the peptide or protein encoded by the nucleic acid molecule. In various embodiments, the nucleic acid molecule further comprises elements which mediate transcription of the nucleic acid molecule once the molecule is integrated into the host genome and/or which serve as selection markers.

In certain embodiments, the nucleic acid molecule is transcribed by a polymerase natively encoded in the host genome. In various embodiments, the nucleic acid molecule is transcribed by a RNA-polymerase which is non-native to the host genome. In such embodiments, the nucleic acid molecule may further comprise a sequence encoding for a polymerase and/or the host genome may be engineered or the host cell may be infected to comprise a nucleic acid sequence encoding for an exogenous polymerase. The host cell may be specifically chosen as a host cell capable of expressing the gene. In addition or otherwise, in order to produce the isolated polypeptide, the nucleic acid coding for it can be genetically engineered for expression in a suitable system. Transformation can be performed using standard techniques (Sambrook, J. et al. (2001), Molecular Cloning: A Laboratory Manual, 3rd Ed., Cold Spring Harbor Laboratory Press, Cold Spring Harbor, NY).

Prokaryotic or eukaryotic host organisms comprising such a vector for recombinant expression of the polypeptide as described herein form also part. Suitable host cells can be prokaryotic cells. In certain embodiments the host cells are selected from the group consisting of gram positive and gram negative bacteria. In some embodiments, the host cell is a gram negative bacterium, such as *E. coli*. In certain embodiments, the host cell is *E. coli*, in particular *E. coli* BL21 (DE3) or other *E. coli* K12 or *E. coli* B834 derivatives. In further embodiments, the host cell is selected from the group consisting of *Escherichia coli* (*E. coli*), *Pseudomonas, Serratia marcescens, Salmonella, Shigella* (and other enterobacteriaceae), *Neisseria, Hemophilus, Klebsiella, Proteus, Enterobacter, Helicobacter, Acinetobacter, Moraxella, Helicobacter, Stenotrophomonas, Bdellovibrio, Legionella*, acetic acid bacteria, *Bacillus, Bacilli, Carynebacterium, Clostridium, Listeria, Streptococcus, Staphylococcus*, and *Archaea* cells. Suitable eukaryotic host cells are among others CHO cells, insect cells, fungi, yeast cells, e.g., *Saccharomyces cerevisiae, S. pombe, Pichia pastoris.*

In certain embodiments, the host cell is a prokaryotic cell, such as *E. coli*, in particular *E. coli* BL21 (DE3), *E. coli* BL21, *E. coli* K12, *E. coli* BLR, *E. coli* BL21 AI, *E. coli* BL21 pLysS, *E. coli* XL1 and *E. coli* DH5a. Further suitable *E. coli* strains include, but are not limited to DH1, DH5a, DM1, HB101, JMIOI-110, Rosetta(DE3)pLysS, SURE, TOP10, XLI-Blue, XL2-Blue and XLIO-Blue strains.

The transformed host cells are cultured under conditions suitable for expression of the nucleotide sequence encoding the polypeptide. In certain embodiments, the cells are cultured under conditions suitable for expression of the nucleotide sequence encoding a polypeptide and, optionally, its secretion.

For producing the recombinant peptide or protein of interest in form of the fusion proteins described herein, a vector can be introduced into a suitable prokaryotic or eukaryotic host organism by means of recombinant DNA technology (as already outlined above). For this purpose, the host cell is first transformed with a vector comprising a nucleic acid molecule using established standard methods (Sambrook, J. et al. (2001), supra). The host cell is then cultured under conditions, which allow expression of the heterologous DNA and thus the synthesis of the corresponding polypeptide. Subsequently, the polypeptide is recovered either from the cell or from the cultivation medium.

For expression of the peptides and proteins several suitable protocols are known to the skilled person. The expression of a recombinant polypeptide may be achieved by the following method comprising: (a) introducing a nucleic acid molecule or vector into a host cell, wherein the nucleic acid molecule or vector encodes the recombinant polypeptide; and (b) cultivating the host cell in a culture medium under conditions that allow expression of the recombinant polypeptide.

Step (a) may be carried out by using suitable transformation and transfection techniques known to those skilled in the art. These techniques are usually selected based on the type of host cell into which the nucleic acid is to be introduced. In some embodiments, the transformation may be achieved using electroporation or heat shock treatment of the host cell.

Step (b) may include a cultivation step that allows growth of the host cells. Alternatively, such step allowing growth of the host cells and a step that allows expression of the polypeptide may be performed separately in that the cells are first cultivated such that they grow to a desired density and then they are cultivated under conditions that allow expression of the polypeptide. The expression step can however still allow growth of the cells.

The method may further include a step of recovering the expressed polypeptide. The polypeptide may be recovered from the growth medium, if it is secreted, or from the cells or both. The recovery of the polypeptide may include various purification steps.

Generally, any known culture medium suitable for growth of the selected host may be employed in this method. In various embodiments, the medium is a rich medium or a minimal medium. Also contemplated herein is a method, wherein the steps of growing the cells and expressing the peptide or protein comprise the use of different media. For example, the growth step may be performed using a rich medium which is replaced by a minimal medium in the expression step. In certain cases, the medium is selected from the group consisting of LB medium, TB medium, 2YT medium, synthetical medium and minimal medium.

In some embodiments, glycerol is added to the culture medium in concentrations of 0.1 v/v % to up to 50 v/v %. The addition of glycerol to the growth medium may positively influence the amount of secreted peptide or protein, if secretion is desired. Without wishing to be bound to a specific theory, it is believed that the folding rate of the recombinantly expressed polypeptides in the cytoplasm of the expression host cell is reduced due to the presence of glycerol in the culture medium. As the intracellular peptide or protein folding rate is reduced, the secretion efficiency is increased.

In some embodiments, the above method further comprises the secretion of the recombinant polypeptide into the culture medium by cultivating the host cell under conditions that allow secretion of the recombinant polypeptide into the culture medium. The term "conditions that allow secretion of the recombinant polypeptide into the culture medium" means that the temperature and medium are chosen such that the polypeptide is secreted. In certain embodiments, this involves supplementing the medium with an inducer of protein expression or changing a physical parameter to induce the protein expression. For example, if the vector encoding for the polypeptide of interest is constructed such that the sequence encoding for the polypeptide of interest is under transcriptional control, the addition of a substrate which releases the suppression of the transcriptional control may be added to the medium or the culture conditions may be reset to induce transcription. Thus, in some embodiments, the medium may be supplemented with IPTG, arabinose, tryptophan and/or maltose, and/or the culture temperature may be changed and/or the culture may be exposed to UV light. In various embodiments, the conditions that allow secretion of the recombinant polypeptide are the same used for the expression of the polypeptide.

Furthermore, in various embodiments where secretion is desired, the host cell may express the other components of the T1 SS, in particular TolC, HlyB, and HlyD. The use of the type 1 secretion system may ensure that the polypeptide is directly secreted to the extracellular space without an intermediate step in the periplasm so that the exposure of the expressed peptide or protein to proteases is avoided.

The other components of the T1 SS may include HlyB and HlyD. In some cases, the two proteins are endogenously expressed, whereas in other cases the two proteins are recombinantly expressed. In the latter case, the nucleic acid molecules encoding for HlyB and/or HlyD may be comprised in the vector harboring the nucleic acid molecule. Alternatively, both proteins are encoded together in one or two additional vectors. For example, HlyB and HlyD may be encoded in a single expression vector which comprises several integration sites for encoding nucleic acid sequences. Such a vector may also comprise a nucleic acid molecule. Suitable vectors may be Duet vectors (Novagen) or derivatives thereof. The above-mentioned one or two additional vectors may comprise selection markers which are the same or different from the selection marker of the vector. Host cells comprising the desired combination of expression vectors can be easily selected if the selection markers of the employed vectors are different from each other.

In some embodiments, if the host cell does not endogenously express TolC, a nucleic acid molecule encoding for TolC may also be comprised in one of the vectors comprised in the host cell or be introduced in the host with an additional vector. In certain embodiments, if the expression and secretion of the recombinant polypeptide is desired, the host cell expresses HlyB, HlyD and TolC in addition to the recombinant peptide or protein. This allows for secretion of the recombinant peptide or protein.

In some embodiments, the entire culture of the host cell, e.g., during growth and expression, is carried out in minimal medium. In various embodiments, the method comprises secretion of the recombinant polypeptide and during secretion the host cell may be cultivated in minimal medium. Minimal medium is advantageous if the recombinant polypeptide is secreted, as the protein, lipid, carbohydrate, pigment, and impurity content in this medium is reduced and thus circumvents or reduces the need of extensive purification steps.

Furthermore, supplementation of the culture medium with alkaline earth metal salts may be advantageous for secretion of the recombinant polypeptide. For an improvement of the secretion, the medium may be complemented at least during secretion or during the entire cell cultivation with at least one alkaline earth metal salt. In some embodiments, the final concentration in the medium is in the range of 1-40 mM. In certain embodiments, the secretion medium may be complemented with at least one alkaline earth metal salt selected from the group consisting of a magnesium salt, calcium salt, strontium salt, or barium salt. In some embodiments, the secretion medium comprises 1-40 mM of a calcium salt. The total concentration of 1-40 mM earth alkaline metal salt may be achieved by combining several salts from different earth alkaline metals and/or the same earth alkaline metal. If the earth alkaline metal is selected from magnesium salt, calcium salt, strontium salt, or barium salt, the composition may comprise 1-40 mM of a single calcium, strontium or barium salt or combinations of several magnesium, calcium, strontium or barium salts, leading to a total concentration in the range of 1-40 mM. In particular, a calcium salt concentration in the range of 1-40 mM may be achieved by combining several calcium salts leading to a total concentration of 1-40 mM. In certain embodiments, the calcium salts are selected from the group consisting of $CaCl_2$), $CaCO_3$, $Ca(OH)_2$, $CaSO_4\ 2H_2O$, $Ca_3(PO4)_2$, $Ca(CH_3COO)_2\ H_2O$, and $Ca(C_2H_3O_2)_2$. In one specific embodiment, the medium contains 1-40 mM $Ca^{2+}$ ions. The medium supplemented accordingly, may be the medium used in the cultivation step that allows expression and/or secretion of the polypeptide.

In particular, if the recombinant polypeptide comprises one or more GG repeats of SEQ ID NO:1, the secretion efficiency is significantly raised if the medium is supplemented with earth alkaline metal salts.

In various embodiments where secretion is desired, the first amino acid sequence comprises the C-terminal end of SEQ ID NO:1, in particular at least the 10 C-terminal amino acids, preferably at least the 20 C-terminal amino acids, more preferably at least the 30 C-terminal amino acids, most preferably at least the 40, at least the 50 or at least the 60 C-terminal amino acids.

In various embodiments, the polypeptide is not secreted. In such embodiments, it may be expressed in form of inclusion bodies. In many cases, it may be useful to express the polypeptide in such an insoluble form, particularly in cases where the peptide of interest is rather short, normally soluble and/or subject to proteolytic degradation within the host cell. Production of the peptide in insoluble form both facilitates simple recovery and protects the peptide from the undesirable proteolytic degradation. In such embodiments, the first amino acid sequence may serve as a solubility tag, i.e., an inclusion body (IB) tag, that induces IB formation. In various such embodiments, the first amino acid sequence may comprise at least one GG repeat sequence, as defined above. Calcium ion (or earth alkaline metal ion) binding to the GG repeat(s) may later catalyze the folding of the fusion polypeptide into the native, active conformation with the calcium ions acting as a folding helper/chaperone.

The terms "inclusion body" or "IB", as interchangeably used herein, relate to nuclear or cytoplasmic aggregates of substances, for instance proteins. IBs are undissolved and have a non-unit lipid membrane. In the method, the IBs mainly consist of the fusion protein comprising at least one peptide/protein of interest and the amino acid sequence derived from SEQ ID NO:1, as defined herein.

In various embodiments, in particular where expression of the polypeptide in form of IBs is desired, the expression of the endogenous ABC transporter gene, the endogenous MFP gene and/or the endogenous OMP gene of the T1 SS or the activity of the corresponding gene products in the host cell is inhibited. In various embodiments, the host cell does not express endogenous ABC transporter, endogenous MFP and/or endogenous OMP of the T1 SS. This may include embodiments where any one or all of TolC, HlyB, and HlyD are not expressed by the host cell. The host cell may be engineered accordingly.

Methods to inhibit the expression of genes such as their deletion or insertion of nucleotide sequences destroying the integrity of the promoter sequence or the gene itself are known in the art. A preferred gene expression activity after deletion or disruption may be less than 35%, 30%, 25%, 20%, 15%, 10% or 5% of the activity measured in untreated cells. In other various embodiments, the endogenous ABC transporter, the endogenous MFP and/or the endogenous OMP of the type 1 secretion system are inhibited by antibodies or small molecule inhibitors. In preferred embodiments, the ABC transporter activity is inhibited by ortho-vanadate or an ATP homologous inhibitor such as 8-azido-ATP. Such ATP mimetics are known in the art. The preferred protein activity after inhibitor treatment may be less than 35%, 30%, 25%, 20%, 15%, 10% or 5% of the activity measured in untreated cells. In other embodiments, the transport is inhibited or blocked by the polypeptide itself, for example by over-expressing it.

In various embodiments of the afore-mentioned methods, the polypeptide is recovered from the host cells in form of insoluble inclusion bodies, for example by any of the purification methods disclosed herein.

The advantages of such a strategy for expression of a fusion protein in form of inclusion bodies are set forth in greater detail in WO 2014/170430 A1, which is herewith included by reference in its entirety.

In various embodiments, the method also encompasses the purification the recombinant polypeptide, wherein the recombinant polypeptide is purified using a method selected from affinity chromatography, ion exchange chromatography, reverse phase chromatography, size exclusion chromatography, and combinations thereof.

In several embodiments, the method may comprise the treatment of the recombinant polypeptide with a protease suitable for cleavage of a protease cleavage site within the recombinant polypeptide. In some embodiments, the recombinant polypeptide is purified prior to proteolytic cleavage using one or more methods disclosed above. Also after cleavage of the recombinant peptide or protein, the method may comprise a further purification step as defined above. Thus, in some embodiments the recombinant polypeptide is purified, subjected to proteolytic cleavage and the peptide or protein of interest is further purified.

In a further aspect, a vector or nucleic acid molecule as disclosed herein may be used for the expression of a recombinant polypeptide. In some embodiments, the vector is used for the expression and secretion of a recombinant polypeptide. The expression or expression and secretion may be achieved using the method described herein.

A method for expression of a recombinant peptide or protein using the above-described nucleic acid molecules may comprise the steps of:

(a) introducing a nucleic acid molecule or a vector as described above into a suitable host cell, wherein the nucleic acid molecule or vector encodes the recombinant polypeptide; and
(b) cultivating the host cell in a culture medium under conditions that allow expression of the recombinant polypeptide and optionally secretion of the recombinant polypeptide into the culture medium.

The method can further be defined as the other methods described above. Specifically, the method may further comprise recovering the expressed peptide or protein from the host cell and/or the culture medium. In addition, the host cell may be a prokaryotic cell; and/or the host cell may express HlyB and HlyD; and/or the expression may be performed in minimal culture medium; and/or the culture medium may comprise 1-40 mM of earth alkaline metal ions, such as $Ca^{2+}$; and/or the recombinant polypeptide may be purified using a method selected from affinity chromatography, ion exchange chromatography, reverse phase chromatography, size exclusion chromatography, and combinations thereof; and/or the method may comprises treatment of the recombinant polypeptide with a protease suitable for cleavage of a protease cleavage site within the recombinant polypeptide; and/or the method may comprise a cleavage step followed by purification of the recombinant polypeptide.

In various embodiments, the polypeptide is recovered in form of inclusion bodies and, after purification, exposed to a refolding buffer, wherein the refolding buffer comprises at least 0.01, more preferably 0.01-40 mM of earth alkaline metal ions, such as $Ca^{2+}$.

EXAMPLES

Materials and Methods

Expression host: *Escherichia coli* BL21 (DE3) (Novagen)

All oligonucleotides were purchased from Microsynth Seqlab GmbH.

Codon optimized nucleotide sequences encoding peptides were purchased from Thermo Fisher Scientific. All enzymes were purchased from NEB, Clontech, Invitrogen or Fermentas.

Expression Protocol

1. Transformation of chemically competent cells with an expression vector encoding for a truncated variant of SEQ ID NO:1 and, optionally, the peptide of interest (as a fusion protein) and plating of the transformed cells on LB agar plates comprising suitable antibiotic(s) for selection of the transformed cells.
2. Incubation of the agar plates over night at 37° C.
3. Inoculation of 2YT medium comprising antibiotics with a single colony from the agar plate for an overnight culture.
4. Incubation at 37° C. and shaking of the culture over night.
5. Inoculation of the main culture comprising 2×YT medium (16 g tryptone/peptone from casein (Roth, #8952.2), 10 g yeast extract (Roth, #2363.2), 5 g NaCl (Roth, #3957.1), ad 1 L demineralized water with the overnight culture resulting in an OD600 of 0.01-0.2 (flasks with baffles)
6. Incubation of the culture at 37° C. at different rpm
7. Induction of the expression the peptide or protein of interest with 1 mM IPTG at an OD600 of 0.4-1.0.
8. Incubation of the cultures for 3 hrs.
9. Culture samples were taken at 0 hrs and 3 hrs post induction and centrifuged for 10 min., 13,000×g, RT.

10. Cell samples were resuspended in water to adjust an OD of 5.0, mixed 4:1 with 5×SDS loading dye and heated (95° C., 10 min).
11. 20 μL samples were loaded on 15% SDS-PAGE gels and SDS-PAGE analysis was performed at 160 V for about 45 min.

Expression and Secretion Protocol

1. Transformation of chemically competent cells with an expression vector encoding for the peptide or protein of interest fused to a secretion substrate, e.g., pSU-AI+ fusion peptide/protein and plating of the transformed cells on LB agar plates comprising suitable antibiotic(s) for selection of the transformed cells, e.g., ampicillin and kanamycin.
2. Incubation over night at 37° C.
3. Inoculation of 2YT medium comprising antibiotics with a single colony for an overnight culture.
4. Incubation at 37° C. and shaking of the culture over night.
5. Inoculation of the main culture and optionally 5 mM $CaCl_2$) with the overnight culture resulting in an OD600 of 0.01-0.2 (flasks+/−baffles, depending on the protein to be secreted)
6. Incubation of the culture at 37° C. at different rpm, depending on the identity of the peptide or protein of interest.
7. Induction of the expression of the peptide or protein of interest fused to a secretion substrate and of the transport complex—consisting of HlyB and HlyD, encoded by pSJ37 or pK184 HlyB, D (TolC, the third protein of this transport complex is consecutively endogenously expressed in *E. coli*) with 1 mM IPTG at an OD600 of 0.4-1-0-
8. Incubation of the cultures for 4-8 hrs, depending on the protein to be secreted.
9. Optionally: centrifugation of the cells for 30 min at 50.000 g and 4° C.
10. Concentration of the cell-free medium.
11. Optionally: Chromatographic purification via FPLC using a size-exclusion column (Superdex 75 16/60) to separate remaining components of the medium.

Example 1: Cloning and Expression of HlyA1 Fragments

The cloning of the various plasmids with HlyA1 truncations is based on the parental plasmid pSU-HlyA1 (SEQ ID NO:31). DNA fragments were amplified by Q5 High-Fidelity DNA Polymerase (according to the NEB protocol), digested with DpnI (according to the NEB protocol) and purified with SpeedBeads (DeAngelis M., Wang D. and Hawkins, T. 1995. Solid-phase reversible immobilization for the isolation of PCR products. Nucleic Acids Res. 23: 4742-4743.).

Plasmids were Created Using Two Cloning Strategies:

Cloning strategy 1: The amplification of a DNA fragment and linearization by phosphorylation and ligation (protocol according to NEB). Example: Primer 1 (SEQ ID NO:32) and Primer 2 (SEQ ID NO:33) were used to generate construct 1.

Cloning strategy 2: The amplification of one or more DNA fragments with 15 bp complementary 5' elongations which are linearized via Gibson reactions (Gibson, D. et al., 2009. Enzymatic assembly of DNA molecules up to several hundred kilobases. Nature Methods, 6: 343-5.). Example: Primer 3 (SEQ ID NO:34) and Primer 4 (SEQ ID NO:35) were used to amplify the plasmid backbone for construct 2. Primer 5 (SEQ ID NO:36) and primer 6 (SEQ ID NO:37) were used to amplify the DNA insert for construct 2.

Exemplary constructs were constructs 1-46 (Polypeptide sequences SEQ ID Nos: 8-26, 44-63, and 65-71).

The expression of said HlyA1 fragments per se and, optionally, as fusion proteins with either one of the peptides having SEQ ID NO:28 (peptide 1), SEQ ID NO:29 (peptide 2) or SEQ ID NO:30 (peptide 3) or another stable antimicrobial peptide (peptide 4; 67 amino acids long, pl 5.69; Mw 7.6 kDa) was quantified by PAGE. The results are shown in Table 1.

TABLE 1

| Construct | w/o peptide of interest | +peptide 1 (SEQ ID NO: 28) | +peptide 2 (SEQ ID NO: 29) | +peptide 3 (SEQ ID NO: 30) | +peptide 4 |
|---|---|---|---|---|---|
| 1 (SEQ ID NO: 8) | − | + | n.d. | + | n.d. |
| 2 (SEQ ID NO: 9) | ++ | ++ | ++ | ++ | n.d. |
| 3 (SEQ ID NO: 10) | ++ | n.d. | ++ | n.d. | n.d. |
| 4 (SEQ ID NO: 11) | ++ | ++ | n.d. | ++ | n.d. |
| 5 (SEQ ID NO: 12) | ++ | n.d. | n.d. | n.d. | n.d. |
| 6 (SEQ ID NO: 13) | ++ | ++ | n.d. | n.d. | n.d. |
| 7 (SEQ ID NO: 14) | + | ++ | n.d. | ++ | n.d. |
| 8 (SEQ ID NO: 15) | ++ | ++ | n.d. | n.d. | n.d. |
| 9 (SEQ ID NO: 16) | + | ++ | ++ | ++ | n.d. |
| 10 (SEQ ID NO: 17) | ++ | n.d. | ++ | + | n.d. |
| 11 (SEQ ID NO: 18) | ++ | + | + | + | n.d. |
| 12 (SEQ ID NO: 19) | + | n.d. | n.d. | + | n.d. |
| 13 (SEQ ID NO: 20) | − | ++ | ++ | ++ | n.d. |
| 14 (SEQ ID NO: 21) | ++ | ++ | ++ | ++ | n.d. |
| 15 (SEQ ID NO: 22) | +/− | ++ | ++ | ++ | n.d. |
| 16 (SEQ ID NO: 23) | +/− | + | + | + | n.d. |
| 17 (SEQ ID NO: 24) | +/− | n.d. | n.d. | n.d. | n.d. |
| 18 (SEQ ID NO: 25) | + | n.d. | n.d. | n.d. | n.d. |
| 19 (SEQ ID NO: 26) | +/− | n.d. | n.d. | n.d. | n.d. |
| 20 (SEQ ID NO: 44) | n.d. | n.d. | n.d. | n.d. | + |
| 21 (SEQ ID NO: 45) | n.d. | n.d. | n.d. | n.d. | + |
| 22 (SEQ ID NO: 46) | n.d. | n.d. | n.d. | n.d. | + |
| 23 (SEQ ID NO: 47) | n.d. | n.d. | n.d. | n.d. | + |
| 24 (SEQ ID NO: 48) | n.d. | n.d. | n.d. | n.d. | + |
| 25 (SEQ ID NO: 49) | n.d. | n.d. | n.d. | n.d. | + |
| 26 (SEQ ID NO: 50) | n.d. | n.d. | n.d. | n.d. | + |

TABLE 1-continued

| Construct | w/o peptide of interest | +peptide 1 (SEQ ID NO: 28) | +peptide 2 (SEQ ID NO: 29) | +peptide 3 (SEQ ID NO: 30) | +peptide 4 |
|---|---|---|---|---|---|
| 27 (SEQ ID NO: 51) | n.d. | n.d. | n.d. | n.d. | + |
| 28 (SEQ ID NO: 52) | n.d. | n.d. | n.d. | n.d. | + |
| 29 (SEQ ID NO: 53) | n.d. | n.d. | n.d. | n.d. | + |
| 30 (SEQ ID NO: 54) | n.d. | n.d. | n.d. | n.d. | +/− |
| 31 (SEQ ID NO: 55) | n.d. | n.d. | n.d. | n.d. | +/− |
| 32 (SEQ ID NO: 56) | n.d. | n.d. | n.d. | n.d. | +/− |
| 33 (SEQ ID NO: 57) | n.d. | n.d. | n.d. | n.d. | +/− |
| 34 (SEQ ID NO: 58) | n.d. | n.d. | n.d. | n.d. | +/− |
| 35 (SEQ ID NO: 59) | n.d. | n.d. | n.d. | n.d. | +/− |
| 36 (SEQ ID NO: 60) | n.d. | n.d. | n.d. | n.d. | +/− |
| 37 (SEQ ID NO: 61) | n.d. | n.d. | n.d. | n.d. | +/− |
| 38 (SEQ ID NO: 62) | n.d. | n.d. | n.d. | n.d. | − |
| 39 (SEQ ID NO: 63) | n.d. | n.d. | n.d. | n.d. | − |
| 40 (SEQ ID NO: 65) | n.d. | n.d. | n.d. | n.d. | + |
| 41 (SEQ ID NO: 66) | n.d. | n.d. | n.d. | n.d. | + |
| 42 (SEQ ID NO: 67) | n.d. | n.d. | n.d. | n.d. | + |
| 43 (SEQ ID NO: 68) | n.d. | n.d. | n.d. | n.d. | + |
| 44 (SEQ ID NO: 69) | n.d. | n.d. | n.d. | n.d. | + |
| 45 (SEQ ID NO: 70) | n.d. | n.d. | n.d. | n.d. | + |
| 46 (SEQ ID NO: 71) | n.d. | n.d. | n.d. | n.d. | + |

"−" = decreased relative to HlyA1 (SEQ ID NO: 1)
"+/−" = similar to HlyA1 (SEQ ID NO: 1)
"+" = increased relative to HlyA1 (SEQ ID NO: 1)
"++" = strongly increased relative to HlyA1 (SEQ ID NO: 1)
n.d. = not determined All documents cited herein, are hereby incorporated by reference in their entirety. The embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A polypeptide variant comprising a first amino acid sequence, wherein the first amino acid sequence comprises:

30 to 202 amino acids in length; and at least 80% sequence identity over its entire length with an amino acid sequence comprised in the amino acid sequence set forth in SEQ ID NO: 1 (HlyA1), wherein the polypeptide variant does not include the full amino acid sequence as set forth in SEQ ID NO: 1, does not include the C-terminal amino acid motif TTSA (SEQ ID NO:27), and comprises a truncation, such that the construct lacks the amino acids corresponding with positions 215-218 of SEQ ID NO:1, wherein the first amino acid sequence comprises any one or more of the amino acid sequence motifs set forth in SEQ ID NO:2 (GNSLA), SEQ ID NO:3 (LKGGYG-NDIYRYLSGYGH), SEQ ID NO:5 (RNWFEKESGDISNHQIEQIFDKSGRIITP), SEQ ID NO:38 (GGKGNDKLY), SEQ ID NO:39 (GGEGD-DLLK), SEQ ID NO:40 (GGYGNDIYR), SEQ ID NO:41 (GGKGNDKLYSEGADLLDGGEGDDLLK), SEQ ID NO:42 (GEGDDLLKGGYGNDIYR), and SEQ ID NO:43 (GGKGNDKLYG SEGADLL-DGGEGDDLLKGGYGNDIYR), wherein the first amino acid sequence further comprises any one or more of the amino acid sequence motifs set forth in SEQ ID NO:4 (RNWF), SEQ ID NO:6 (LAYGS), and SLLQLSGNASDESYGRNSITL (SEQ ID NO:7).

2. The polypeptide variant of claim 1, wherein the polypeptide variant comprises less than 203 continuous amino acids of the amino acid sequence set forth in SEQ ID NO:1.

3. The polypeptide variant of claim 1, wherein the first amino acid sequence is derived from the amino acid sequence set forth in SEQ ID NO: 1 by any one or more of an N-terminal truncation, or a deletion of one or more amino acids.

4. The polypeptide variant of claim 1, wherein the first amino acid sequence comprises the amino acid motif(s) of:

(i) SEQ ID NO: 5;
(ii) SEQ ID NOs: 5 and 6;
(iii) SEQ ID NOs: 5, 6 and 7;
(iv) SEQ ID NO: 3;
(v) SEQ ID NOs: 3 and 4;
(vi) SEQ ID NOs: 2 and 3;
(vii) SEQ ID NOs: 2 and 5;
(viii) SEQ ID NOs: 2, 6 and 7;
(ix) SEQ ID NOs: 2, 5 and 6;
(x) SEQ IN NOs: 2, 5, 6 and 7;
(xi) SEQ ID NOs: 2, 3 and 4;
(xii) SEQ ID NOs: 2, 3 and 5;
(xiii) SEQ ID NO:38;
(xiv) SEQ ID NO:39;
(XV) SEQ ID NO:40;
(xvi) SEQ ID NO:41;
(xvii) SEQ ID NO:42;
(xviii) SEQ ID NO:43;
(xix) SEQ ID NOs: 2 and 38;
(xx) SEQ ID NOs: 2 and 39;
(xxi) SEQ ID NOs: 2 and 40;
(xxii) SEQ ID NOs: 2 and 41;
(xxiii) SEQ ID NOs: 2 and 42; or
(xxiv) SEQ ID NOs: 2 and 43.

5. The polypeptide variant of claim 1, wherein the polypeptide variant comprises a second amino acid sequence N-terminal or C-terminal to the first amino acid sequence, wherein the second amino acid sequence encodes for at least one peptide or polypeptide of interest.

6. The polypeptide variant of claim 5, wherein the second amino acid sequence is directly or via an optional linker sequence linked to the N- or C-terminal end of the first amino acid sequence, wherein the optional linker sequence is 1 to 30 amino acids in length.

7. The polypeptide variant of claim 6, wherein the optional linker sequence comprises a protease recognition and cleavage site.

8. The polypeptide variant of claim 5, wherein the second amino acid sequence is 10 to 500 amino acids in length.

9. The polypeptide variant of claim 5, further comprising at least one third amino acid sequence, optionally at least one affinity tag.

10. The polypeptide variant of claim 1, wherein the polypeptide variant has, relative to a polypeptide comprising the full length sequence of SEQ ID NO:1 as the first amino acid sequence, an equal or increased expression in a host cell under identical expression conditions.

11. A nucleic acid molecule encoding the polypeptide variant of claim 1.

12. A vector comprising the nucleic acid molecule according to claim 11.

13. A host cell comprising the nucleic acid molecule according to claim 11, wherein the host cell is a prokaryotic host cell.

14. A method for the production of the polypeptide variant of claim 1, wherein the method comprises:

cultivating a host cell comprising a nucleic acid molecule that encodes the polypeptide variant under conditions that allow the expression of the polypeptide variant; and isolating the expressed polypeptide variant from the host cell.

* * * * *

SEQUENCE LISTING

```
<160> NUMBER OF SEQ ID NOS: 72

<210> SEQ ID NO 1
<211> LENGTH: 218
<212> TYPE: PRT
<213> ORGANISM: Artificial
<220> FEATURE:
<223> OTHER INFORMATION: Fragment of HlyA (HlyA1)

<400> SEQUENCE: 1

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60
```

```
Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe Asp Val Lys Glu Glu Arg Thr Ala
            180                 185                 190

Ala Ser Leu Leu Gln Leu Ser Gly Asn Ala Ser Asp Phe Ser Tyr Gly
        195                 200                 205

Arg Asn Ser Ile Thr Leu Thr Thr Ser Ala
    210                 215


<210> SEQ ID NO 2
<211> LENGTH: 5
<212> TYPE: PRT
<213> ORGANISM: Artificial
<220> FEATURE:
<223> OTHER INFORMATION: HlyA motif

<400> SEQUENCE: 2

Gly Asn Ser Leu Ala
1               5


<210> SEQ ID NO 3
<211> LENGTH: 18
<212> TYPE: PRT
<213> ORGANISM: Artificial
<220> FEATURE:
<223> OTHER INFORMATION: HlyA motif

<400> SEQUENCE: 3

Leu Lys Gly Gly Tyr Gly Asn Asp Ile Tyr Arg Tyr Leu Ser Gly Tyr
1               5                   10                  15

Gly His


<210> SEQ ID NO 4
<211> LENGTH: 4
<212> TYPE: PRT
<213> ORGANISM: Artificial
<220> FEATURE:
<223> OTHER INFORMATION: HlyA motif

<400> SEQUENCE: 4

Arg Asn Trp Phe
1


<210> SEQ ID NO 5
<211> LENGTH: 29
<212> TYPE: PRT
<213> ORGANISM: Artificial
<220> FEATURE:
<223> OTHER INFORMATION: HlyA motif
```

<400> SEQUENCE: 5

```
Arg Asn Trp Phe Glu Lys Glu Ser Gly Asp Ile Ser Asn His Gln Ile
1               5                   10                  15

Glu Gln Ile Phe Asp Lys Ser Gly Arg Ile Ile Thr Pro
            20                  25
```

<210> SEQ ID NO 6
<211> LENGTH: 5
<212> TYPE: PRT
<213> ORGANISM: Artificial
<220> FEATURE:
<223> OTHER INFORMATION: HlyA motif

<400> SEQUENCE: 6

```
Leu Ala Tyr Gly Ser
1               5
```

<210> SEQ ID NO 7
<211> LENGTH: 21
<212> TYPE: PRT
<213> ORGANISM: Artificial
<220> FEATURE:
<223> OTHER INFORMATION: HlyA motif

<400> SEQUENCE: 7

```
Ser Leu Leu Gln Leu Ser Gly Asn Ala Ser Asp Phe Ser Tyr Gly Arg
1               5                   10                  15

Asn Ser Ile Thr Leu
            20
```

<210> SEQ ID NO 8
<211> LENGTH: 113
<212> TYPE: PRT
<213> ORGANISM: Artificial
<220> FEATURE:
<223> OTHER INFORMATION: HlyA fragment

<400> SEQUENCE: 8

```
Arg Asn Trp Phe Glu Lys Glu Ser Gly Asp Ile Ser Asn His Gln Ile
1               5                   10                  15

Glu Gln Ile Phe Asp Lys Ser Gly Arg Ile Ile Thr Pro Asp Ser Leu
            20                  25                  30

Lys Lys Ala Leu Glu Tyr Gln Gln Arg Asn Asn Lys Ala Ser Tyr Val
        35                  40                  45

Tyr Gly Asn Asp Ala Leu Ala Tyr Gly Ser Gln Gly Asp Leu Asn Pro
    50                  55                  60

Leu Ile Asn Glu Ile Ser Lys Ile Ile Ser Ala Ala Gly Ser Phe Asp
65                  70                  75                  80

Val Lys Glu Glu Arg Thr Ala Ala Ser Leu Leu Gln Leu Ser Gly Asn
                85                  90                  95

Ala Ser Asp Phe Ser Tyr Gly Arg Asn Ser Ile Thr Leu Thr Thr Ser
            100                 105                 110

Ala
```

<210> SEQ ID NO 9
<211> LENGTH: 163
<212> TYPE: PRT
<213> ORGANISM: Artificial
<220> FEATURE:
<223> OTHER INFORMATION: HlyA fragment

<400> SEQUENCE: 9

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Asp Lys Leu Ser
            20                  25                  30

Leu Ala Asp Ile Asp Phe Arg Asp Val Ala Phe Lys Arg Glu Gly Asn
        35                  40                  45

Asp Leu Ile Ala Tyr Lys Ala Glu Gly Asn Val Leu Ser Ile Gly His
    50                  55                  60

Lys Asn Gly Ile Thr Phe Arg Asn Trp Phe Glu Lys Glu Ser Gly Asp
65                  70                  75                  80

Ile Ser Asn His Gln Ile Glu Gln Ile Phe Asp Lys Ser Gly Arg Ile
                85                  90                  95

Ile Thr Pro Asp Ser Leu Lys Leu Ala Tyr Gly Ser Gln Gly Asp Leu
            100                 105                 110

Asn Pro Leu Ile Asn Glu Ile Ser Lys Ile Ile Ser Ala Ala Gly Ser
        115                 120                 125

Phe Asp Val Lys Glu Glu Arg Thr Ala Ala Ser Leu Leu Gln Leu Ser
    130                 135                 140

Gly Asn Ala Ser Asp Phe Ser Tyr Gly Arg Asn Ser Ile Thr Leu Thr
145                 150                 155                 160

Thr Ser Ala
```

<210> SEQ ID NO 10
<211> LENGTH: 158
<212> TYPE: PRT
<213> ORGANISM: Artificial
<220> FEATURE:
<223> OTHER INFORMATION: HlyA fragment

<400> SEQUENCE: 10

```
Gly Asn Ser Leu Ala Leu Lys Gly Gly Tyr Gly Asn Asp Ile Tyr Arg
1               5                   10                  15

Tyr Leu Ser Gly Tyr Gly His Asp Lys Leu Ser Leu Ala Asp Ile Asp
            20                  25                  30

Phe Arg Asp Val Ala Phe Lys Arg Glu Gly Asn Asp Leu Ile Ala Tyr
        35                  40                  45

Lys Ala Glu Gly Asn Val Leu Ser Ile Gly His Lys Asn Gly Ile Thr
    50                  55                  60

Phe Arg Asn Trp Phe Glu Lys Glu Ser Gly Asp Ile Ser Asn His Gln
65                  70                  75                  80

Ile Glu Gln Ile Phe Asp Lys Ser Gly Arg Ile Ile Thr Pro Asp Ser
                85                  90                  95

Leu Lys Leu Ala Tyr Gly Ser Gln Gly Asp Leu Asn Pro Leu Ile Asn
            100                 105                 110

Glu Ile Ser Lys Ile Ile Ser Ala Ala Gly Ser Phe Asp Val Lys Glu
        115                 120                 125

Glu Arg Thr Ala Ala Ser Leu Leu Gln Leu Ser Gly Asn Ala Ser Asp
    130                 135                 140

Phe Ser Tyr Gly Arg Asn Ser Ile Thr Leu Thr Thr Ser Ala
145                 150                 155
```

<210> SEQ ID NO 11
<211> LENGTH: 153
<212> TYPE: PRT
<213> ORGANISM: Artificial
<220> FEATURE:

<223> OTHER INFORMATION: HlyA fragment

<400> SEQUENCE: 11

```
Gly Asn Ser Leu Ala Leu Lys Gly Gly Tyr Gly Asn Asp Ile Tyr Arg
1               5                   10                  15

Tyr Leu Ser Gly Tyr Gly His Asp Lys Leu Ser Leu Ala Asp Ile Asp
            20                  25                  30

Phe Arg Asp Val Ala Phe Lys Arg Glu Gly Asn Asp Leu Ile Ala Tyr
        35                  40                  45

Lys Ala Glu Gly Asn Val Leu Ser Ile Gly His Lys Asn Gly Ile Thr
    50                  55                  60

Phe Arg Asn Trp Phe Glu Lys Glu Ser Gly Asp Ile Ser Asn His Gln
65                  70                  75                  80

Ile Glu Gln Ile Phe Asp Lys Ser Gly Arg Ile Ile Thr Pro Asp Ser
                85                  90                  95

Leu Lys Leu Ala Tyr Gly Ser Gln Gly Asp Leu Asn Pro Leu Ile Asn
            100                 105                 110

Glu Ile Ser Lys Ile Ile Ser Ala Ala Gly Ser Phe Asp Val Lys Glu
        115                 120                 125

Glu Arg Thr Ala Ala Ser Leu Leu Gln Leu Ser Gly Asn Ala Ser Asp
    130                 135                 140

Phe Ser Tyr Gly Arg Asn Ser Ile Thr
145                 150
```

<210> SEQ ID NO 12
<211> LENGTH: 148
<212> TYPE: PRT
<213> ORGANISM: Artificial
<220> FEATURE:
<223> OTHER INFORMATION: HlyA fragment

<400> SEQUENCE: 12

```
Gly Asn Ser Leu Ala Leu Lys Gly Gly Tyr Gly Asn Asp Ile Tyr Arg
1               5                   10                  15

Tyr Leu Ser Gly Tyr Gly His Asp Lys Leu Ser Leu Ala Asp Ile Asp
            20                  25                  30

Phe Arg Asp Val Ala Phe Lys Arg Glu Gly Asn Asp Leu Ile Ala Tyr
        35                  40                  45

Lys Ala Glu Gly Asn Val Leu Ser Ile Gly His Lys Asn Gly Ile Thr
    50                  55                  60

Phe Arg Asn Trp Phe Glu Lys Glu Ser Gly Asp Ile Ser Asn His Gln
65                  70                  75                  80

Ile Glu Gln Ile Phe Asp Lys Ser Gly Arg Ile Ile Thr Pro Asp Ser
                85                  90                  95

Leu Lys Leu Ala Tyr Gly Ser Pro Leu Ile Asn Glu Ile Ser Lys Ile
            100                 105                 110

Ile Ser Ala Ala Gly Ser Phe Asp Val Lys Glu Glu Arg Thr Ala Ala
        115                 120                 125

Ser Leu Leu Gln Leu Ser Gly Asn Ala Ser Asp Phe Ser Tyr Gly Arg
    130                 135                 140

Asn Ser Ile Thr
145
```

<210> SEQ ID NO 13
<211> LENGTH: 143
<212> TYPE: PRT
<213> ORGANISM: Artificial

<220> FEATURE:
<223> OTHER INFORMATION: HlyA fragment

<400> SEQUENCE: 13

```
Gly Asn Ser Leu Ala Leu Lys Gly Gly Tyr Gly Asn Asp Ile Tyr Arg
1               5                   10                  15

Tyr Leu Ser Gly Tyr Gly His Asp Lys Leu Ser Leu Ala Asp Ile Asp
            20                  25                  30

Phe Arg Asp Val Ala Phe Lys Arg Glu Gly Asn Asp Leu Ile Ala Tyr
        35                  40                  45

Lys Ala Glu Gly Asn Val Leu Ser Ile Gly His Lys Asn Gly Ile Thr
    50                  55                  60

Phe Arg Asn Trp Phe Glu Lys Glu Ser Gly Asp Ile Ser Asn His Gln
65                  70                  75                  80

Ile Glu Gln Ile Phe Asp Lys Ser Gly Arg Ile Ile Thr Pro Asp Ser
                85                  90                  95

Leu Lys Leu Ala Tyr Gly Ser Ile Ser Lys Ile Ile Ser Ala Ala Gly
            100                 105                 110

Ser Phe Asp Val Lys Glu Glu Arg Thr Ala Ala Ser Leu Leu Gln Leu
        115                 120                 125

Ser Gly Asn Ala Ser Asp Phe Ser Tyr Gly Arg Asn Ser Ile Thr
    130                 135                 140
```

<210> SEQ ID NO 14
<211> LENGTH: 133
<212> TYPE: PRT
<213> ORGANISM: Artificial
<220> FEATURE:
<223> OTHER INFORMATION: HlyA fragment

<400> SEQUENCE: 14

```
Gly Asn Ser Leu Ala Leu Lys Gly Gly Tyr Gly Asn Asp Ile Tyr Arg
1               5                   10                  15

Tyr Leu Ser Gly Tyr Gly His Asp Lys Leu Ser Leu Ala Asp Ile Asp
            20                  25                  30

Phe Arg Asp Val Ala Phe Lys Arg Glu Gly Asn Asp Leu Ile Ala Tyr
        35                  40                  45

Lys Ala Glu Gly Asn Val Leu Ser Ile Gly His Lys Asn Gly Ile Thr
    50                  55                  60

Phe Arg Asn Trp Phe Glu Lys Glu Ser Gly Asp Ile Ser Asn His Gln
65                  70                  75                  80

Ile Glu Gln Ile Phe Asp Lys Ser Gly Arg Ile Ile Thr Pro Asp Ser
                85                  90                  95

Leu Lys Leu Ala Tyr Gly Ser Phe Asp Val Lys Glu Glu Arg Thr Ala
            100                 105                 110

Ala Ser Leu Leu Gln Leu Ser Gly Asn Ala Ser Asp Phe Ser Tyr Gly
        115                 120                 125

Arg Asn Ser Ile Thr
    130
```

<210> SEQ ID NO 15
<211> LENGTH: 148
<212> TYPE: PRT
<213> ORGANISM: Artificial
<220> FEATURE:
<223> OTHER INFORMATION: HlyA fragment

<400> SEQUENCE: 15

```
Gly Asn Ser Leu Ala Leu Lys Gly Gly Tyr Gly Asn Asp Ile Tyr Arg
1               5                   10                  15

Tyr Leu Ser Gly Tyr Gly His Asp Lys Leu Ser Leu Ala Asp Ile Asp
            20                  25                  30

Phe Arg Asp Val Ala Phe Lys Arg Glu Gly Asn Asp Leu Ile Ala Tyr
        35                  40                  45

Lys Ala Glu Gly Asn Val Leu Ser Ile Gly His Lys Asn Gly Ile Thr
    50                  55                  60

Phe Arg Asn Trp Phe Glu Lys Glu Ser Gly Asp Ile Ser Asn His Gln
65                  70                  75                  80

Ile Glu Gln Ile Phe Asp Lys Ser Gly Arg Ile Ile Thr Pro Asp Ser
                85                  90                  95

Leu Lys Leu Ala Tyr Gly Ser Ile Ser Lys Ile Ile Ser Ala Ala Gly
            100                 105                 110

Ser Phe Asp Val Lys Glu Glu Arg Thr Ala Ala Ser Leu Leu Gln Leu
        115                 120                 125

Ser Gly Asn Ala Ser Asp Phe Ser Tyr Gly Arg Asn Ser Ile Thr Leu
    130                 135                 140

Thr Thr Ser Ala
145


<210> SEQ ID NO 16
<211> LENGTH: 128
<212> TYPE: PRT
<213> ORGANISM: Artificial
<220> FEATURE:
<223> OTHER INFORMATION: HlyA fragment

<400> SEQUENCE: 16

Gly Asn Ser Leu Ala Leu Lys Gly Gly Tyr Gly Asn Asp Ile Tyr Arg
1               5                   10                  15

Tyr Leu Ser Gly Tyr Gly His Asp Lys Leu Ser Leu Ala Asp Ile Asp
            20                  25                  30

Phe Arg Asp Val Ala Phe Lys Arg Glu Gly Asn Asp Leu Ile Ala Tyr
        35                  40                  45

Lys Ala Glu Gly Asn Val Leu Ser Ile Gly His Lys Asn Gly Ile Thr
    50                  55                  60

Phe Arg Asn Trp Phe Glu Lys Glu Ser Gly Asp Ile Ser Asn His Gln
65                  70                  75                  80

Ile Glu Gln Ile Phe Asp Lys Ser Gly Arg Ile Ile Thr Pro Asp Ser
                85                  90                  95

Leu Lys Leu Ala Tyr Gly Ser Ser Leu Leu Gln Leu Ser Gly Asn Ala
            100                 105                 110

Ser Asp Phe Ser Tyr Gly Arg Asn Ser Ile Thr Leu Thr Thr Ser Ala
        115                 120                 125


<210> SEQ ID NO 17
<211> LENGTH: 208
<212> TYPE: PRT
<213> ORGANISM: Artificial
<220> FEATURE:
<223> OTHER INFORMATION: HlyA fragment

<400> SEQUENCE: 17

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30
```

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Ala Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His Gln Ile Glu Gln Ile Phe Asp Lys Ser
115 120 125

Gly Arg Ile Ile Thr Pro Asp Ser Leu Lys Lys Ala Leu Glu Tyr Gln
130 135 140

Gln Arg Asn Asn Lys Ala Ser Tyr Val Tyr Gly Asn Asp Ala Leu Ala
145 150 155 160

Tyr Gly Ser Pro Leu Ile Asn Glu Ile Ser Lys Ile Ile Ser Ala Ala
165 170 175

Gly Ser Phe Asp Val Lys Glu Glu Arg Thr Ala Ala Ser Leu Leu Gln
180 185 190

Leu Ser Gly Asn Ala Ser Asp Phe Ser Tyr Gly Arg Asn Ser Ile Thr
195 200 205

<210> SEQ ID NO 18
<211> LENGTH: 203
<212> TYPE: PRT
<213> ORGANISM: Artificial
<220> FEATURE:
<223> OTHER INFORMATION: HlyA fragment

<400> SEQUENCE: 18

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Ala Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His Gln Ile Glu Gln Ile Phe Asp Lys Ser
115 120 125

Gly Arg Ile Ile Thr Pro Asp Ser Leu Lys Lys Ala Leu Glu Tyr Gln
130 135 140

Gln Arg Asn Asn Lys Ala Ser Tyr Val Tyr Gly Asn Asp Ala Leu Ala
145 150 155 160

Tyr Gly Ser Ile Ser Lys Ile Ile Ser Ala Ala Gly Ser Phe Asp Val
165 170 175

Lys Glu Glu Arg Thr Ala Ala Ser Leu Leu Gln Leu Ser Gly Asn Ala
180 185 190

Ser Asp Phe Ser Tyr Gly Arg Asn Ser Ile Thr
195 200

<210> SEQ ID NO 19
<211> LENGTH: 193
<212> TYPE: PRT
<213> ORGANISM: Artificial
<220> FEATURE:
<223> OTHER INFORMATION: HlyA fragment

<400> SEQUENCE: 19

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Ala Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His Gln Ile Glu Gln Ile Phe Asp Lys Ser
115 120 125

Gly Arg Ile Ile Thr Pro Asp Ser Leu Lys Lys Ala Leu Glu Tyr Gln
130 135 140

Gln Arg Asn Asn Lys Ala Ser Tyr Val Tyr Gly Asn Asp Ala Leu Ala
145 150 155 160

Tyr Gly Ser Phe Asp Val Lys Glu Glu Arg Thr Ala Ala Ser Leu Leu
165 170 175

Gln Leu Ser Gly Asn Ala Ser Asp Phe Ser Tyr Gly Arg Asn Ser Ile
180 185 190

Thr

<210> SEQ ID NO 20
<211> LENGTH: 110
<212> TYPE: PRT
<213> ORGANISM: Artificial
<220> FEATURE:
<223> OTHER INFORMATION: HlyA fragment

<400> SEQUENCE: 20

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Met Tyr Lys Ala Glu Gly Asn Val Leu Ser
85 90 95

```
Ile Gly His Lys Asn Gly Ile Thr Phe Arg Asn Trp Phe Glu
            100                 105                 110


<210> SEQ ID NO 21
<211> LENGTH: 134
<212> TYPE: PRT
<213> ORGANISM: Artificial
<220> FEATURE:
<223> OTHER INFORMATION: HlyA fragment

<400> SEQUENCE: 21

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro
    130


<210> SEQ ID NO 22
<211> LENGTH: 164
<212> TYPE: PRT
<213> ORGANISM: Artificial
<220> FEATURE:
<223> OTHER INFORMATION: HlyA fragment

<400> SEQUENCE: 22

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
```

145 150 155 160

Tyr Gly Ser Gln

<210> SEQ ID NO 23
<211> LENGTH: 184
<212> TYPE: PRT
<213> ORGANISM: Artificial
<220> FEATURE:
<223> OTHER INFORMATION: HlyA fragment

<400> SEQUENCE: 23

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Met Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His Gln Ile Glu Gln Ile Phe Asp Lys Ser
115 120 125

Gly Arg Ile Ile Thr Pro Asp Ser Leu Lys Lys Ala Leu Glu Tyr Gln
130 135 140

Gln Arg Asn Asn Lys Ala Ser Tyr Val Tyr Gly Asn Asp Ala Leu Ala
145 150 155 160

Tyr Gly Ser Gln Gly Asp Leu Asn Pro Leu Ile Asn Glu Ile Ser Lys
165 170 175

Ile Ile Ser Ala Ala Gly Ser Phe
180

<210> SEQ ID NO 24
<211> LENGTH: 205
<212> TYPE: PRT
<213> ORGANISM: Artificial
<220> FEATURE:
<223> OTHER INFORMATION: HlyA fragment

<400> SEQUENCE: 24

Gly Asn Ser Leu Ala Tyr Gly Ser Glu Gly Ala Asp Leu Leu Asp Gly
1 5 10 15

Gly Glu Gly Asp Asp Leu Leu Lys Gly Gly Tyr Gly Asn Asp Ile Tyr
20 25 30

Arg Tyr Leu Ser Gly Tyr Gly His His Ile Ile Asp Asp Asp Gly Gly
35 40 45

Lys Glu Asp Lys Leu Ser Leu Ala Asp Ile Asp Phe Arg Asp Val Ala
50 55 60

Phe Lys Arg Glu Gly Asn Asp Leu Ile Met Tyr Lys Ala Glu Gly Asn
65 70 75 80

Val Leu Ser Ile Gly His Lys Asn Gly Ile Thr Phe Arg Asn Trp Phe
85 90 95

Glu Lys Glu Ser Gly Asp Ile Ser Asn His Gln Ile Glu Gln Ile Phe

```
            100                 105                 110

Asp Lys Ser Gly Arg Ile Ile Thr Pro Asp Ser Leu Lys Lys Ala Leu
        115                 120                 125

Glu Tyr Gln Gln Arg Asn Asn Lys Ala Ser Tyr Val Tyr Gly Asn Asp
    130                 135                 140

Ala Leu Ala Tyr Gly Ser Gln Gly Asp Leu Asn Pro Leu Ile Asn Glu
145                 150                 155                 160

Ile Ser Lys Ile Ile Ser Ala Ala Gly Ser Phe Asp Val Lys Glu Glu
                165                 170                 175

Arg Thr Ala Ala Ser Leu Leu Gln Leu Ser Gly Asn Ala Ser Asp Phe
            180                 185                 190

Ser Tyr Gly Arg Asn Ser Ile Thr Leu Thr Thr Ser Ala
        195                 200                 205


<210> SEQ ID NO 25
<211> LENGTH: 188
<212> TYPE: PRT
<213> ORGANISM: Artificial
<220> FEATURE:
<223> OTHER INFORMATION: HlyA fragment

<400> SEQUENCE: 25

Gly Asn Ser Leu Ala Leu Lys Gly Gly Tyr Gly Asn Asp Ile Tyr Arg
1               5                   10                  15

Tyr Leu Ser Gly Tyr Gly His His Ile Ile Asp Asp Asp Gly Gly Lys
            20                  25                  30

Glu Asp Lys Leu Ser Leu Ala Asp Ile Asp Phe Arg Asp Val Ala Phe
        35                  40                  45

Lys Arg Glu Gly Asn Asp Leu Ile Ala Tyr Lys Ala Glu Gly Asn Val
    50                  55                  60

Leu Ser Ile Gly His Lys Asn Gly Ile Thr Phe Arg Asn Trp Phe Glu
65                  70                  75                  80

Lys Glu Ser Gly Asp Ile Ser Asn His Gln Ile Glu Gln Ile Phe Asp
                85                  90                  95

Lys Ser Gly Arg Ile Ile Thr Pro Asp Ser Leu Lys Lys Ala Leu Glu
            100                 105                 110

Tyr Gln Gln Arg Asn Asn Lys Ala Ser Tyr Val Tyr Gly Asn Asp Ala
        115                 120                 125

Leu Ala Tyr Gly Ser Gln Gly Asp Leu Asn Pro Leu Ile Asn Glu Ile
    130                 135                 140

Ser Lys Ile Ile Ser Ala Ala Gly Ser Phe Asp Val Lys Glu Glu Arg
145                 150                 155                 160

Thr Ala Ala Ser Leu Leu Gln Leu Ser Gly Asn Ala Ser Asp Phe Ser
                165                 170                 175

Tyr Gly Arg Asn Ser Ile Thr Leu Thr Thr Ser Ala
            180                 185


<210> SEQ ID NO 26
<211> LENGTH: 155
<212> TYPE: PRT
<213> ORGANISM: Artificial
<220> FEATURE:
<223> OTHER INFORMATION: HlyA fragment

<400> SEQUENCE: 26

Gly Asn Ser Leu Ala Ala Asp Ile Asp Phe Arg Asp Val Ala Phe Lys
1               5                   10                  15
```

Arg Glu Gly Asn Asp Leu Ile Ala Tyr Lys Ala Glu Gly Asn Val Leu
20 25 30

Ser Ile Gly His Lys Asn Gly Ile Thr Phe Arg Asn Trp Phe Glu Lys
35 40 45

Glu Ser Gly Asp Ile Ser Asn His Gln Ile Glu Gln Ile Phe Asp Lys
50 55 60

Ser Gly Arg Ile Ile Thr Pro Asp Ser Leu Lys Lys Ala Leu Glu Tyr
65 70 75 80

Gln Gln Arg Asn Asn Lys Ala Ser Tyr Val Tyr Gly Asn Asp Ala Leu
85 90 95

Ala Tyr Gly Ser Gln Gly Asp Leu Asn Pro Leu Ile Asn Glu Ile Ser
100 105 110

Lys Ile Ile Ser Ala Ala Gly Ser Phe Asp Val Lys Glu Glu Arg Thr
115 120 125

Ala Ala Ser Leu Leu Gln Leu Ser Gly Asn Ala Ser Asp Phe Ser Tyr
130 135 140

Gly Arg Asn Ser Ile Thr Leu Thr Thr Ser Ala
145 150 155

<210> SEQ ID NO 27
<211> LENGTH: 4
<212> TYPE: PRT
<213> ORGANISM: Artificial
<220> FEATURE:
<223> OTHER INFORMATION: HlyA motif

<400> SEQUENCE: 27

Thr Thr Ser Ala
1

<210> SEQ ID NO 28
<211> LENGTH: 31
<212> TYPE: PRT
<213> ORGANISM: Artificial
<220> FEATURE:
<223> OTHER INFORMATION: Peptide of interest 1

<400> SEQUENCE: 28

His Ala Glu Gly Thr Phe Thr Ser Asp Val Ser Ser Tyr Leu Glu Gly
1 5 10 15

Gln Ala Ala Lys Glu Phe Ile Ala Trp Leu Val Arg Gly Arg Gly
20 25 30

<210> SEQ ID NO 29
<211> LENGTH: 18
<212> TYPE: PRT
<213> ORGANISM: Artificial
<220> FEATURE:
<223> OTHER INFORMATION: Peptide of interest 2

<400> SEQUENCE: 29

Lys Trp Cys Phe Arg Val Cys Tyr Arg Gly Ile Cys Tyr Arg Arg Cys
1 5 10 15

Arg Asp

<210> SEQ ID NO 30
<211> LENGTH: 29
<212> TYPE: PRT
<213> ORGANISM: Artificial
<220> FEATURE:
<223> OTHER INFORMATION: Peptide of interest 3

<400> SEQUENCE: 30

Glu Gly Thr Phe Thr Ser Asp Val Ser Ser Tyr Leu Glu Gly Gln Ala
1 5 10 15

Ala Lys Glu Phe Ile Ala Trp Leu Val Arg Gly Arg Gly
20 25

<210> SEQ ID NO 31
<211> LENGTH: 4545
<212> TYPE: DNA
<213> ORGANISM: Artificial
<220> FEATURE:
<223> OTHER INFORMATION: pSU HlyA1 vector

<400> SEQUENCE: 31
tgattacgaa ttcgagctcc caaaactcat gttggtaaag tatcagaatt tcatggaggt 60
aaaattgata aacagttagc gaataaaatt tttaaacaat atcaccacga gttaataact 120
gaagtaaaaa gaaagtcaga ttttaatttt tcattaactg gttaagaggt aattaaatgg 180
gaaattctct tgcaaaaaat gtattattcg gtggaaaagg taatgacaag ctgtacggca 240
gtgagggggc agatctgctt gatggtggag agggggatga tctcctgaaa ggcggatatg 300
gtaatgatat ttatcgttat ctgtcaggat atggtcatca tattattgat gatgatgggg 360
ggaaagagga taaactcagt ttggctgata ttgatttccg ggatgtggcc ttcaagcgag 420
aaggtaatga cctcatcatg tataaagctg aaggtaatgt tctttccatt ggtcataaaa 480
atggtattac attcaggaac tggtttgaaa aagagtcagg tgatatctct aatcaccaga 540
tagagcagat tttgataaa agtggccgga taatcacacc tgattccctt aaaaaggcac 600
ttgagtatca acagcgtaat aataaggcaa gttatgtgta tgggaatgat gcattagcct 660
atggaagtca gggtgatctt aatccattaa ttaatgaaat cagcaaaatc atttcagctg 720
caggtagctt cgatgttaaa gaggaaagaa ctgcagcttc tttattgcag ttgtccggta 780
atgccagtga tttttcatat ggacggaact caataaccct gaccacatca gcataatata 840
ttaatttaaa tgatagcaat cttactgggc tgtgccacat aagattgcta ttttttttgg 900
agtcataatg gattcttgtc ataaaattga ttatgggtta tacgccctgg agattttagc 960
ccaataccat aacgtctctg ttaacccgga agaaattaaa catagatttg atacagacgg 1020
gacaggtctg ggattaacgt catggttgct tgctgcgaaa tctttagaac taaaggtaaa 1080
acaggtaaaa aaaacaattg atcgatgata agctgtcaaa catgagaatt acaacttata 1140
tcgtatgggg ctgacttcag gtgctacatt tgaagagata aattgcactg aaatcctgca 1200
ggcatgcaag cttggcactg gccgtcgttt tacaacgtcg tgactgggaa aaccctggcg 1260
ttacccaact taatcgcctt gcagcacatc cccctttcgc cagctggcgt aatagcgaag 1320
aggcccgcac cgatcgccct tcccaacagt tgcgcagcct gaatggcgaa tgccgttaac 1380
ggattcttga agacgaaagg gcctcgtgat acgcctattt ttataggtta atgtcatgat 1440
aataatggtt tcttagacgt caggtggcac ttttcgggga aatgtgcgcg gaacccctat 1500
ttgtttattt ttctaaatac attcaaatat gtatccgctc atgagacaat aaccctgata 1560
aatgcttcaa taatattgaa aaaggaagag tatgagtatt caacatttcc gtgtcgccct 1620
tattcccttt tttgcggcat tttgccttcc tgtttttgct cacccagaaa cgctggtgaa 1680
agtaaaagat gctgaagatc agttgggtgc acgagtgggt tacatcgaac tggatctcaa 1740
cagcggtaag atccttgaga gttttcgccc cgaagaacgt tttccaatga tgagcacttt 1800
taaagttctg ctatgtggcg cggtattatc ccgtattgac gccgggcaag agcaactcgg 1860

```
tcgccgcata cactattctc agaatgactt ggttgagtac tcaccagtca cagaaaagca   1920
tcttacggat ggcatgacag taagagaatt atgcagtgct gccataacca tgagtgataa   1980
cactgcggcc aacttacttc tgacaacgat cggaggaccg aaggagctaa ccgctttttt   2040
gcacaacatg ggggatcatg taactcgcct tgatcgttgg gaaccggagc tgaatgaagc   2100
cataccaaac gacgagcgtg acaccacgat gcctgtagca atggcaacaa cgttgcgcaa   2160
actattaact ggcgaactac ttactctagc ttcccggcaa caattaatag actggatgga   2220
ggcggataaa gttgcaggac cacttctgcg ctcggccctt ccggctggct ggtttattgc   2280
tgataaatct ggagccggtg agcgtgggtc tcgcggtatc attgcagcac tggggccaga   2340
tggtaagccc tcccgtatcg tagttatcta cacgacgggg agtcaggcaa ctatggatga   2400
acgaaataga cagatcgctg agataggtgc ctcactgatt aagcattggt aactgtcaga   2460
ccaagtttac tcatatatac tttagattga tttaaaactt catttttaat ttaaaaggat   2520
ctaggtgaag atcctttttg ataatctcat gaccaaaatc ccttaacgtg agttttcgtt   2580
ccactgagcg tcagaccccg tagaaaagat caaaggatct tcttgagatc cttttttct    2640
gcgcgtaatc tgctgcttgc aaacaaaaaa accaccgcta ccagcggtgg tttgtttgcc   2700
ggatcaagag ctaccaactc tttttccgaa ggtaactggc ttcagcagag cgcagatacc   2760
aaatactgtc cttctagtgt agccgtagtt aggccaccac ttcaagaact ctgtagcacc   2820
gcctacatac ctcgctctgc taatcctgtt accagtggct gctgccagtg gcgataagtc   2880
gtgtcttacc gggttggact caagacgata gttaccggat aaggcgcagc ggtcgggctg   2940
aacggggggt tcgtgcacac agcccagctt ggagcgaacg acctacaccg aactgagata   3000
cctacagcgt gagctatgag aaagcgccac gcttcccgaa gggagaaagg cggacaggta   3060
tccggtaagc ggcagggtcg gaacaggaga gcgcacgagg gagcttccag ggggaaacgc   3120
ctggtatctt tatagtcctg tcgggtttcg ccacctctga cttgagcgtc gatttttgtg   3180
atgctcgtca ggggggcgga gcctatggaa aaacgccagc aacgcggcct ttttacggtt   3240
cctggccttt tgctggcctt ttgctcacat gttctttcct gcgttatccc ctgattctgt   3300
ggataaccgt attaccgcct ttgagtgagc tgataccgct cgccgcagcc gaacgaccga   3360
gcgcagcgag tcagtgagcg aggaagcgga agagcgcctg atgcggtatt ttctccttac   3420
gcatctgtgc ggtatttcac accgcatatg gtgcactctc agtacaatct gctctgatgc   3480
cgcatagtta agccagtata cactccgcta tcgctacgtg actgggtcat ggctgcgccc   3540
cgacacccgc caacacccgc tgacgcgccc tgacgggctt gtctgctccc ggcatccgct   3600
tacagacaag ctgtgaccgt ctccgggagc tgcatgtgtc agaggttttc accgtcatca   3660
ccgaaacgcg cgaggcagct gcggtaaagc tcatcagcgt ggtcgtgaag cgattcacag   3720
atgtctgcct gttcatccgc gtccagctcg ttgagtttct ccagaagcgt taatgtctgg   3780
cttctgataa agcgggccat gttaagggcg gttttttcct gtttggtcac tgatgcctcc   3840
gtgtaagggg gatttctgtt catgggggta atgataccga tgaaacgaga gaggatgctc   3900
acgatacggg ttactgatga tgaacatgcc cggttactgg aacgttgtga gggtaaacaa   3960
ctggcggtat ggatgcggcg ggaccagaga aaaatcactc agggtcaatg ccagcgcttc   3HI
gttaatacag atgtaggtgt tccacagggt agccagcagc atcctgcgat gcagatccgg   4080
aacataatgg tgcagggcgc tgacttccgc gtttccagac tttacgaaac acggaaaccg   4140
aagaccattc atgttgttgc tcaggtcgca gacgttttgc agcagcagtc gcttcacgtt   4200
```

```
cgctcgcgta tcggtgattc attctgctaa ccagtaaggc aaccccgcca gcctagccgg   4260

gtcctcaacg acaggagcac gatcatgcgc acccgtggcc aggacccaac gctgcccgcc   4320

gttaacggcc aatacgcaaa ccgcctctcc ccgcgcgttg gccgattcat taatgcagct   4380

ggcacgacag gtttcccgac tggaaagcgg gcagtgagcg caacgcaatt aatgtgagtt   4440

agctcactca ttaggcaccc caggctttac actttatgct tccggctcgt atgttgtgtg   4500

gaattgtgag cggataacaa tttcacacag gaaacagcta tgaca                   4545


<210> SEQ ID NO 32
<211> LENGTH: 41
<212> TYPE: DNA
<213> ORGANISM: Artificial
<220> FEATURE:
<223> OTHER INFORMATION: Oligonucleotide primer

<400> SEQUENCE: 32

catttaatta cctcttaacc agttaatgaa aaattaaaat c                         41


<210> SEQ ID NO 33
<211> LENGTH: 21
<212> TYPE: DNA
<213> ORGANISM: Artificial
<220> FEATURE:
<223> OTHER INFORMATION: Oligonucleotide primer

<400> SEQUENCE: 33

aggaactggt ttgaaaaaga g                                               21


<210> SEQ ID NO 34
<211> LENGTH: 33
<212> TYPE: DNA
<213> ORGANISM: Artificial
<220> FEATURE:
<223> OTHER INFORMATION: Oligonucleotide primer

<400> SEQUENCE: 34

caaactgagt ttatcatcaa gcagatctgc ccc                                  33


<210> SEQ ID NO 35
<211> LENGTH: 22
<212> TYPE: DNA
<213> ORGANISM: Artificial
<220> FEATURE:
<223> OTHER INFORMATION: Oligonucleotide primer

<400> SEQUENCE: 35

ttagcctatg gaagtcaggg tg                                              22


<210> SEQ ID NO 36
<211> LENGTH: 34
<212> TYPE: DNA
<213> ORGANISM: Artificial
<220> FEATURE:
<223> OTHER INFORMATION: Oligonucleotide primer

<400> SEQUENCE: 36

gataaactca gtttggctga tattgatttc cggg                                 34


<210> SEQ ID NO 37
<211> LENGTH: 34
<212> TYPE: DNA
<213> ORGANISM: Artificial
<220> FEATURE:
<223> OTHER INFORMATION: Oligonucleotide primer
```

<400> SEQUENCE: 37
acttccatag gctaatttaa gggaatcagg tgtg 34

<210> SEQ ID NO 38
<211> LENGTH: 9
<212> TYPE: PRT
<213> ORGANISM: Artificial
<220> FEATURE:
<223> OTHER INFORMATION: HlyA1 GG repeat 1

<400> SEQUENCE: 38

Gly Gly Lys Gly Asn Asp Lys Leu Tyr
1 5

<210> SEQ ID NO 39
<211> LENGTH: 9
<212> TYPE: PRT
<213> ORGANISM: Artificial
<220> FEATURE:
<223> OTHER INFORMATION: HlyA1 GG repeat 2

<400> SEQUENCE: 39

Gly Gly Glu Gly Asp Asp Leu Leu Lys
1 5

<210> SEQ ID NO 40
<211> LENGTH: 9
<212> TYPE: PRT
<213> ORGANISM: Artificial
<220> FEATURE:
<223> OTHER INFORMATION: HlyA1 GG repeat 3

<400> SEQUENCE: 40

Gly Gly Tyr Gly Asn Asp Ile Tyr Arg
1 5

<210> SEQ ID NO 41
<211> LENGTH: 26
<212> TYPE: PRT
<213> ORGANISM: Artificial
<220> FEATURE:
<223> OTHER INFORMATION: HlyA motif

<400> SEQUENCE: 41

Gly Gly Lys Gly Asn Asp Lys Leu Tyr Ser Glu Gly Ala Asp Leu Leu
1 5 10 15

Asp Gly Gly Glu Gly Asp Asp Leu Leu Lys
20 25

<210> SEQ ID NO 42
<211> LENGTH: 18
<212> TYPE: PRT
<213> ORGANISM: Artificial
<220> FEATURE:
<223> OTHER INFORMATION: HlyA motif

<400> SEQUENCE: 42

Gly Gly Glu Gly Asp Asp Leu Leu Lys Gly Gly Tyr Gly Asn Asp Ile
1 5 10 15

Tyr Arg

<210> SEQ ID NO 43
<211> LENGTH: 36
<212> TYPE: PRT

<213> ORGANISM: Artificial
<220> FEATURE:
<223> OTHER INFORMATION: HlyA motif

<400> SEQUENCE: 43

Gly Gly Lys Gly Asn Asp Lys Leu Tyr Gly Ser Glu Gly Ala Asp Leu
1 5 10 15

Leu Asp Gly Gly Glu Gly Asp Asp Leu Leu Lys Gly Gly Tyr Gly Asn
20 25 30

Asp Ile Tyr Arg
35

<210> SEQ ID NO 44
<211> LENGTH: 134
<212> TYPE: PRT
<213> ORGANISM: Artificial
<220> FEATURE:
<223> OTHER INFORMATION: HlyA1 truncation del135-218

<400> SEQUENCE: 44

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Met Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His Gln Ile Glu Gln Ile Phe Asp Lys Ser
115 120 125

Gly Arg Ile Ile Thr Pro
130

<210> SEQ ID NO 45
<211> LENGTH: 129
<212> TYPE: PRT
<213> ORGANISM: Artificial
<220> FEATURE:
<223> OTHER INFORMATION: HlyA1 truncation del130-218

<400> SEQUENCE: 45

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Met Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His Gln Ile Glu Gln Ile Phe Asp Lys Ser
115 120 125

Gly

<210> SEQ ID NO 46
<211> LENGTH: 124
<212> TYPE: PRT
<213> ORGANISM: Artificial
<220> FEATURE:
<223> OTHER INFORMATION: HlyA1 truncation del125-218

<400> SEQUENCE: 46

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Met Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His Gln Ile Glu Gln Ile
115 120

<210> SEQ ID NO 47
<211> LENGTH: 119
<212> TYPE: PRT
<213> ORGANISM: Artificial
<220> FEATURE:
<223> OTHER INFORMATION: HlyA1 truncation del120-218

<400> SEQUENCE: 47

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Met Tyr Lys Ala Glu Gly Asn Val Leu Ser
85 90 95

Ile Gly His Lys Asn Gly Ile Thr Phe Arg Asn Trp Phe Glu Lys Glu
100 105 110

Ser Gly Asp Ile Ser Asn His
115

<210> SEQ ID NO 48

<211> LENGTH: 114
<212> TYPE: PRT
<213> ORGANISM: Artificial
<220> FEATURE:
<223> OTHER INFORMATION: HlyA1 truncation del115-218

<400> SEQUENCE: 48

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly
```

<210> SEQ ID NO 49
<211> LENGTH: 109
<212> TYPE: PRT
<213> ORGANISM: Artificial
<220> FEATURE:
<223> OTHER INFORMATION: HlyA1 truncation del110-218

<400> SEQUENCE: 49

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe
            100                 105
```

<210> SEQ ID NO 50
<211> LENGTH: 104
<212> TYPE: PRT
<213> ORGANISM: Artificial
<220> FEATURE:
<223> OTHER INFORMATION: HlyA1 truncation del105-218

<400> SEQUENCE: 50

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
```

```
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr
            100
```

```
<210> SEQ ID NO 51
<211> LENGTH: 99
<212> TYPE: PRT
<213> ORGANISM: Artificial
<220> FEATURE:
<223> OTHER INFORMATION: HlyA1 truncation del100-218

<400> SEQUENCE: 51

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His
```

```
<210> SEQ ID NO 52
<211> LENGTH: 94
<212> TYPE: PRT
<213> ORGANISM: Artificial
<220> FEATURE:
<223> OTHER INFORMATION: HlyA1 truncation del95-218

<400> SEQUENCE: 52

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val
                85                  90
```

```
<210> SEQ ID NO 53
<211> LENGTH: 89
<212> TYPE: PRT
<213> ORGANISM: Artificial
<220> FEATURE:
<223> OTHER INFORMATION: HlyA1 truncation del90-218
```

<400> SEQUENCE: 53

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys
                85

<210> SEQ ID NO 54
<211> LENGTH: 84
<212> TYPE: PRT
<213> ORGANISM: Artificial
<220> FEATURE:
<223> OTHER INFORMATION: HlyA1 truncation del85-218

<400> SEQUENCE: 54

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp

<210> SEQ ID NO 55
<211> LENGTH: 79
<212> TYPE: PRT
<213> ORGANISM: Artificial
<220> FEATURE:
<223> OTHER INFORMATION: HlyA1 truncation del80-218

<400> SEQUENCE: 55

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys
65                  70                  75

<210> SEQ ID NO 56
<211> LENGTH: 74
<212> TYPE: PRT
<213> ORGANISM: Artificial
<220> FEATURE:

<223> OTHER INFORMATION: HlyA1 truncation del75-218

<400> SEQUENCE: 56

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg
65 70

<210> SEQ ID NO 57
<211> LENGTH: 69
<212> TYPE: PRT
<213> ORGANISM: Artificial
<220> FEATURE:
<223> OTHER INFORMATION: HlyA1 truncation del70-218

<400> SEQUENCE: 57

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala
65

<210> SEQ ID NO 58
<211> LENGTH: 64
<212> TYPE: PRT
<213> ORGANISM: Artificial
<220> FEATURE:
<223> OTHER INFORMATION: HlyA1 truncation del65-218

<400> SEQUENCE: 58

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

<210> SEQ ID NO 59
<211> LENGTH: 59
<212> TYPE: PRT
<213> ORGANISM: Artificial
<220> FEATURE:
<223> OTHER INFORMATION: HlyA1 truncation del60-218

<400> SEQUENCE: 59

Gly Asn Ser Leu Ala Lys Asn Val Leu Phe Gly Gly Lys Gly Asn Asp
1 5 10 15

```
Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp
    50                  55


<210> SEQ ID NO 60
<211> LENGTH: 54
<212> TYPE: PRT
<213> ORGANISM: Artificial
<220> FEATURE:
<223> OTHER INFORMATION: HlyA1 truncation del55-218

<400> SEQUENCE: 60

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His
    50


<210> SEQ ID NO 61
<211> LENGTH: 49
<212> TYPE: PRT
<213> ORGANISM: Artificial
<220> FEATURE:
<223> OTHER INFORMATION: HlyA1 truncation del50-218

<400> SEQUENCE: 61

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser


<210> SEQ ID NO 62
<211> LENGTH: 44
<212> TYPE: PRT
<213> ORGANISM: Artificial
<220> FEATURE:
<223> OTHER INFORMATION: HlyA1 truncation del 45-218

<400> SEQUENCE: 62

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile
        35                  40


<210> SEQ ID NO 63
<211> LENGTH: 39
<212> TYPE: PRT
<213> ORGANISM: Artificial
<220> FEATURE:
<223> OTHER INFORMATION: HlyA1 truncation del 40-218
```

<400> SEQUENCE: 63

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly
35

<210> SEQ ID NO 64
<211> LENGTH: 7
<212> TYPE: PRT
<213> ORGANISM: ARTIFICIAL
<220> FEATURE:
<223> OTHER INFORMATION: TEV protease site
<220> FEATURE:
<221> NAME/KEY: MISC_FEATURE
<222> LOCATION: (7)..(7)
<223> OTHER INFORMATION: Xaa is G, S, A, M or C

<400> SEQUENCE: 64

Glu Asn Leu Tyr Phe Gln Xaa
1 5

<210> SEQ ID NO 65
<211> LENGTH: 110
<212> TYPE: PRT
<213> ORGANISM: Artificial
<220> FEATURE:
<223> OTHER INFORMATION: HlyA1 fragment del111-218

<400> SEQUENCE: 65

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp
50 55 60

Lys Leu Ser Leu Ala Asp Ile Asp Phe Arg Asp Val Ala Phe Lys Arg
65 70 75 80

Glu Gly Asn Asp Leu Ile Met Tyr Lys Ala Glu Gly Asn Val Leu Ser
85 90 95

Ile Gly His Lys Asn Gly Ile Thr Phe Arg Asn Trp Phe Glu
100 105 110

<210> SEQ ID NO 66
<211> LENGTH: 134
<212> TYPE: PRT
<213> ORGANISM: Artificial
<220> FEATURE:
<223> OTHER INFORMATION: HlyA1 fragment del135-218

<400> SEQUENCE: 66

Gly Asn Ser Leu Ala Lys Asn Val Leu Phe Gly Gly Lys Gly Asn Asp
1 5 10 15

Lys Leu Tyr Gly Ser Glu Gly Ala Asp Leu Leu Asp Gly Gly Glu Gly
20 25 30

Asp Asp Leu Leu Lys Gly Gly Tyr Gly Asn Asp Ile Tyr Arg Tyr Leu
35 40 45

Ser Gly Tyr Gly His His Ile Ile Asp Asp Asp Gly Gly Lys Glu Asp

```
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro
    130


<210> SEQ ID NO 67
<211> LENGTH: 164
<212> TYPE: PRT
<213> ORGANISM: Artificial
<220> FEATURE:
<223> OTHER INFORMATION: HlyA1 fragment 165-218

<400> SEQUENCE: 67

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Gln


<210> SEQ ID NO 68
<211> LENGTH: 184
<212> TYPE: PRT
<213> ORGANISM: Artificial
<220> FEATURE:
<223> OTHER INFORMATION: HlyA1 fragment 185-218

<400> SEQUENCE: 68

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
```

```
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe
            180


<210> SEQ ID NO 69
<211> LENGTH: 193
<212> TYPE: PRT
<213> ORGANISM: Artificial
<220> FEATURE:
<223> OTHER INFORMATION: HlyA1 fragment del164-183 del214-218

<400> SEQUENCE: 69

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Phe Asp Val Lys Glu Glu Arg Thr Ala Ala Ser Leu Leu
                165                 170                 175

Gln Leu Ser Gly Asn Ala Ser Asp Phe Ser Tyr Gly Arg Asn Ser Ile
            180                 185                 190

Thr


<210> SEQ ID NO 70
<211> LENGTH: 203
<212> TYPE: PRT
<213> ORGANISM: Artificial
```

```
<220> FEATURE:
<223> OTHER INFORMATION: HlyA1 fragment del164-173 del214-218

<400> SEQUENCE: 70

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Ile Ser Lys Ile Ile Ser Ala Ala Gly Ser Phe Asp Val
                165                 170                 175

Lys Glu Glu Arg Thr Ala Ala Ser Leu Leu Gln Leu Ser Gly Asn Ala
            180                 185                 190

Ser Asp Phe Ser Tyr Gly Arg Asn Ser Ile Thr
        195                 200


<210> SEQ ID NO 71
<211> LENGTH: 208
<212> TYPE: PRT
<213> ORGANISM: Artificial
<220> FEATURE:
<223> OTHER INFORMATION: HlyA1 fragment del164-168 del214-218

<400> SEQUENCE: 71

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
```

-continued

```
    130                 135                 140

Gln Arg Asn Asn Lys Ala Ser Tyr Val Tyr Gly Asn Asp Ala Leu Ala
145                 150                 155                 160

Tyr Gly Ser Pro Leu Ile Asn Glu Ile Ser Lys Ile Ile Ser Ala Ala
                165                 170                 175

Gly Ser Phe Asp Val Lys Glu Glu Arg Thr Ala Ala Ser Leu Leu Gln
            180                 185                 190

Leu Ser Gly Asn Ala Ser Asp Phe Ser Tyr Gly Arg Asn Ser Ile Thr
        195                 200                 205


<210> SEQ ID NO 72
<211> LENGTH: 8
<212> TYPE: PRT
<213> ORGANISM: Artificial
<220> FEATURE:
<223> OTHER INFORMATION: G-rich motif

<400> SEQUENCE: 72

Gly Gly Lys Glu Asp Lys Leu Ser
1               5
```